US008445461B2

(12) United States Patent
Takeda

(10) Patent No.: US 8,445,461 B2
(45) Date of Patent: May 21, 2013

(54) PHARMACEUTICAL COMPOSITION FOR MENIERE'S DISEASE

(75) Inventor: Setsuko Takeda, Hyogo (JP)

(73) Assignee: Setsuko Takeda, Hyogo (JP)

( * ) Notice: Subject to any disclaimer, the term of this patent is extended or adjusted under 35 U.S.C. 154(b) by 599 days.

(21) Appl. No.: 12/448,804

(22) PCT Filed: Jan. 10, 2007

(86) PCT No.: PCT/JP2007/050172
§ 371 (c)(1),
(2), (4) Date: Aug. 24, 2009

(87) PCT Pub. No.: WO2008/084533
PCT Pub. Date: Jul. 17, 2008

(65) Prior Publication Data
US 2010/0120712 A1 May 13, 2010

(51) Int. Cl.
A61K 31/715 (2006.01)
A61K 31/723 (2006.01)
A61K 31/729 (2006.01)
A61K 31/732 (2006.01)

(52) U.S. Cl.
USPC ........... 514/54; 536/2; 536/3; 536/123.12; 536/123.1

(58) Field of Classification Search
None
See application file for complete search history.

(56) References Cited

U.S. PATENT DOCUMENTS

| 4,816,298 | A | * | 3/1989 | Alderman et al. | ............ | 427/212 |
| 5,656,284 | A | * | 8/1997 | Balkin | ............ | 424/435 |
| 5,668,158 | A | | 9/1997 | Fink | | |
| 6,245,820 | B1 | | 6/2001 | Kojima et al. | | |
| 6,372,248 | B1 | * | 4/2002 | Qin et al. | ............ | 424/443 |

FOREIGN PATENT DOCUMENTS

| CN | 101164544 | 4/2008 |
| FR | 2 775 598 | 9/1999 |
| JP | 2007-001964 | 1/2007 |
| JP | 2007-31450 | 2/2007 |
| JP | 2007-230990 | 9/2007 |
| JP | 2008-185628 | 8/2008 |
| JP | 2008-188006 | 8/2008 |
| JP | 2008-189650 | 8/2008 |
| JP | 2008-189651 | 8/2008 |
| JP | 2008-189654 | 8/2008 |
| JP | 2008-231795 | 10/2008 |
| JP | 2008-231796 | 10/2008 |
| WO | 2006/001344 | 1/2006 |
| WO | 2009/116490 | 9/2009 |

OTHER PUBLICATIONS

English machine translation of JP4264105, published Feb. 20, 2009, equivalent to WO2006/001344 published Jan. 5, 2006, downloaded from www.ipdl.inpit.go.jp.*
Takeuchi et al., "Tabletting of Solid Dispersion Particles Consisting of Indomethacin and Porous Silica Particles" Chem Pharm Bull (2005) vol. 53 No. 5 pp. 487-491.*
Kolodziejska, "The Effect of Saccharic Alcohols on Rheological Parameters of Dental Anti-Inflammatory Gels and on Pharmaceutical AVAilability of Sodium Ibuprofen" Acta Poloniae Pharmaceutica—Drug Research (2006) vol. 63 No. 2 pp. 127-133.*
I. Kirikae et al., "Otorhinolaryngology", pp. 160-161, 2004 (Abstract).
A. Komatsuzaki et al., "Clinical Textbooks of the Ear, Nose and Throat Regions 21", Client 21, No. 8, pp. 365-377, 1999 (Abstract).
C. Angelborg et al., "Hyperosmotic Solutions and Hearing in Meniere's Disease", The American Journal of Otology, vol. 3, No. 3, pp. 200-202, Jan. 1982.
T. Takeda et al., "The Rebound Phenomenon of Glycerol-Induced Changes in the Endolymphatic Space", Acta Otolaryngol (Stockh), vol. 119, pp. 341-344, 1999.
H. Matsubara et al., "Rebound Phenomenon in Glycerol Test", Acta Otolaryngol (Stockh), Suppl. 419, pp. 115-122, 1985.
S. Sawada et al., "Aquaporin-1 (AQP1) is expressed in the stria vascularis of rat cochlea", Hearing Research, vol. 181, pp. 15-19, 2003.
S. Sawada et al., "Aquaproin-2 regulation by vasopressin in the rat inner ear", Auditory and Vestibular Systems, vol. 13, No. 9, pp. 1127-1129, Jul. 2002.
T. Takeda et al., "The effects of $V_2$ antagonist (OPC-31260) on endolymphatic hydrops", Hearing Research, vol. 182, pp. 9-18, 2003.
T. Takeda et al., "Antidiuretic Hormone (ADH) and Endolymphatic Hydrops", Acta Otolaryngol (Stockh), Suppl. 519, pp. 219-222, 1995.
T. Takeda et al., "Endolymphatic hydrops induced by chronic administration of vasopressin", Hearing Research, vol. 140, pp. 1-6, 2000.
A. Safwate et al., "Renin-Aldosterone System and Arginine Vasopressin Diarrhoeic Calves", British Veterinary Journal, vol. 147, pp. 533-537, 1991.
A. Kakigi et al., "Time Course of Dehydrating Effects of Isosorbide on Experimentally Induced Endolymphatic Hydrops in Guinea Pigs", ORL, vol. 66, pp. 291-296, 2004.
J. Wiley & Sons, "Encyclopedia of Chemical Technology", Fourth Edition, New York, vol. 4, pp. 911-948, 2001.
K. Kashiba et al., "Study for Making Isosorbide Jelly to Increase Compliance", Clinical Otology, vol. 99, No. 1, pp. 61-65, Jan. 1, 2006.
Journal of the Tokyo Hospital Pharmacists Association, vol. 55, No. 5, pp. 326-328, Oct. 31, 2006.
International Search Report dated Feb. 13, 2007 & English translation of the International Preliminary Report on Patentability.
Chinese Office Action dated Nov. 12, 2010 in Chinese Patent Application No: 200780049682.3 with English translation.
Supplementary European Search Report dated Mar. 29, 2011 in European Application No. 07706519.1.
T. Takeda et al., "Decompression Effects of Erythritol on Endolymphatic Hydrops", Auris Nasus Larynx, vol. 36, No. 2, pp. 146-151, Apr. 1, 2009.

* cited by examiner

Primary Examiner — Eric S Olson

(74) Attorney, Agent, or Firm — Wenderoth, Lind & Ponack, L.L.P.

(57) ABSTRACT

The present invention provides pharmaceutical composition for treating Meniere's disease, comprising saccharides or sugar alcohols as an active ingredient and polysaccharides, wherein the ratio by weight of the saccharides or sugar alcohols to the polysaccharides is about 100:2 to 100:50. The pharmaceutical composition of the present invention may eliminate the cathartic effect caused by saccharides or sugar alcohols to ensure the endolymphatic hydrops decompression effect. Therefore the effect of the therapeutic composition of the present invention is improved. The pharmaceutical composition may provide in gel, powder, granule form or the like.

14 Claims, 11 Drawing Sheets

PHARMACEUTICAL COMPOSITION FOR MENIERE'S DISEASE

PHARMACEUTICAL COMPOSITION FOR MENIERE'S DISEASE

This application is a U.S. national stage of International Application No. PCT/JP2007/050172 filed Jan. 10, 2007.

FIELD OF THE INVENTION

The present invention relates to a pharmaceutical composition for treating Meniere's disease, in particular a pharmaceutical composition for treating Meniere's disease without a cathartic effect as a side-effect, wherein said composition comprises a saccharide or a sugar alcohol as an active ingredient.

BACKGROUND OF THE INVENTION

The etiology of Meniere's disease has not yet been settled. However, as is well known in the art, the characteristic histopathological feature of Meniere's disease is endolymphatic hydrops considering from the histological observation of autopsy specimens from patients with Meniere's disease. It is believed that such endolymphatic hydrops may be induced by the accumulation of endolymphatic fluid due to an aberrant water-metabolism in the inner ear, such as an excess production and/or an impaired absorption of endolymphatic fluid, leading one or more of conditions associated with Meniere's disease, for example, tinnitus, hearing disorder, vertigo, ear fullness or the like. Therefore, it may be understood that decompressing the endolymphatic hydrops may lead the treatment of Meniere's disease.

Most of saccharides and sugar alcohols exhibit an osmotic effect after the administration and have been used as osmotic diuretics or osmotic pressure decreasing agents. As the agents having a dehydrating activity due to the osmotic effect, there are known sorbitol, mannitol, etc., which have a cathartic effect, as well as mannitol, glycerol, etc., which have a diuretic effect. Since the histo-pathological feature of Meniere's disease is endolymphatic hydrops, it appears that hydrops would be decompressed by the dehydrating action. Namely, said agents which produce an osmotic gradient between endolymphatic and perilymphatic compartments are thought to exert a dehydratic effect upon the scala media, and also induce the decompression and/or the collapse of the volume of endolymphatic space and reveal the decompressing effect on endolymphatic hydrops.

Actually, some of saccharides or sugar alcohols as the osmotic diuretics are used for diagnosis of Meniere's disease (cf. Ichiro Kirikae, Otorhinolaryngology, P174, L34-P175, L2; Non-patent Reference 1). During the test, the hearing improvement was observed due to the osmotic diuretics (cf. Atsushi Komatsuzaki, Client 21, P368, right column L23-24; Non-patent Reference 2). Considering these facts, various trials have been made to develop the therapeutic agents.

Contrary to what might be expected, all of trials failed finally, and the riddle for such failure remained unsolved. Angelborg C. et al reported that the improvement of the hearing could only be observed in the half or more cases of the group administered with glycerol (cf. Non-patent Reference 3, P201, Table 1). When, however, guinea pigs orally received glycerol at 2.8 g/kg, the collapse was observed in the normal ear 2 hours after the administration, and the mild hydrops were observed 6 hours after (cf. Non-patent Reference 4); namely, rebound phenomenon was observed morphologically. These results can histologically support the so-called "rebound phenomenon" which is observed in the glycerol test for diagnosis of Meniere's disease as a temporary improvement of hearing 2 hours after the administration and subsequent deterioration 6 hours after (cf. Non-patent Reference 5). Because of rebound phenomenon, glycerol is currently not used as a therapeutic agent in Japan.

Since the 1990s, the presence of water channels was successively confirmed in several organs. In the inner ear having a relatively similar tissue structure to the kidney, the study was developed for elucidation of the mechanisms of water homeostasis, the production and absorption of fluid in inner ear, and the presence of aquaporin (water channel protein) in the inner ear was confirmed (cf. Non-patent Reference 6). Recently, the arginine vasopressin-aquaporin 2 system has widely noticed as the one associated with the water metabolism in the inner ear (cf. Non-patent Reference 7).

However, the systemic administration of OPC 31260 as the vasopressin type II receptor antagonist did not reveal the decompression effect on endolymphatic hydrops as originally expected and rather resulted in formation of endolymphatic hydrops in the normal ear (cf. Non-patent Reference 8). This was found to be due to the dehydration caused by the potent diuretic effect, i.e. the increase of arginine vasopressin (AVP) as the antidiuretic hormone (ADH) in plasma. As understood from the above, many trial-and-error investigations have been made up to this time, but none of them led to the successful outcome applicable to the clinical use.

It was reported that the AVP level is clinically enhanced at an acute phase in patients with Meniere's disease (cf. Non-patent Reference 9). This result is coincident with an epidemiological fact that Meniere's disease is prevalent under stress. Also, the continuous administration of AVP at 1 mU/kg/minute by the aid of a mini-pump subcutaneously to guinea pigs of normal Prayer's reflex apparently produced endolymphatic hydrops (cf. Non-patent Reference 10). As shown in Table 1 below, the plasma AVP level is elevated in proportion to the administration amount of AVP, whereby the area of scala media is increased histologically (formation of endolymphatic hydrops). When AVP is successively administered at 1 mu/kg the serum AVP level is elevated to several times higher than that of normal human plasma AVP level (nearly equal to the serum AVP level at an acute phase in a patient with Meniere's disease), which is at serious risk (cf. Non-patent Reference 10). For treatment of Meniere's disease, special care is needed not to cause the elevation of the AVP level by stress, dehydration or the like.

TABLE 1

| Agent | Plasma AVP | Increase ratio (%) of the cross-sectional area of the scala media |
|---|---|---|
| Saline | 1.2 ± 0.5 | 5.2 ± 1.7 |
| AVP 0.2 mU | 2.2 ± 0.4 | 4.4 ± 0.7 |
| AVP 0.4 mU | 3.5 ± 1.8 | 10.4 ± 1.8 |
| AVP 1.0 mU | 14.0 ± 3.9 | 17.4 ± 7.9 |

(The present inventors, Hearing Res. 2000; Non-patent Reference 10)
Administration rate of AVP: mU/kg/min
Unit of plasma AVP: pg/ml The upper limit of the plasma AVP level for a normal subject is 3.5 pg/ml.

As predicted from the fact that saccharides or sugar alcohols are used as osmotic pressure reducing agents, those basically induce an osmotic gradient in the digestive organ and develop gastrointestinal disorders such as diarrhea when administered orally at a high dose at one time. Even severe diarrhea, which cannot be treated by common gastrointestinal agents, arises frequently. In case of severe diarrhea, it is reported that the dehydration is brought about sequentially and the level of AVP as antidiuretic hormone is elevated to 10-15 times (cf. Non-patent Reference 11). Since elevated AVP level may induce endolymphatic hydrops as stated above, it is conceived that the endolymphatic hydrops decompression effect of saccharides or sugar alcohols may be countered by the dehydration following diarrhea, unless the diarrhea induced by them is successfully inhibited. Accordingly, careful attention should be taken not to aggravate gastrointestinal disorders such as diarrhea, when patients with Meniere's disease are treated with saccharides or sugar alcohols, Patent Reference 1 discloses a pharmaceutical composition for treating Meniere's disease comprising a tetrose such as erythritol as the sole active ingredient. Erythritol is advantageous in having a favorable flavor, but it is reported that transient severe diarrhea was induced on taking a large amount of a sports drink containing erythritol as a low-calorie sweetener within a short period of time. Therefore, the therapeutic effect of erythritol for Meniere's disease can be hardly expected without inhibiting diarrhea, The sugar alcohol currently on the clinical use as a therapeutic agent for Meniere's disease is isosorbide (1,2:3,6-dianhydro-D-sorbitol). Its cathartic effect is relatively weak in a clinical practice but it has a characteristic bitter taste which remains in oral cavity for a long time. In addition, it has to be administered at such a high dose as 30 ml or more each three times per day. Because of these reasons, it causes poor compliance for patients leading to give up taking said substance. Also, it was inconvenient that the dosage form is a solution and the recipients must carry such large volume bottles as 500 ml due to sanitary issues.

In addition, glycerol as a triose exerts its effect about 2 hours after the oral administration, meanwhile isosorbide as a hexose takes as long time as 6 hours or so until exertion of its effect (cf. Non-patent Reference 12).

Patent Reference 1: JP-A-11-180863;
Non-patent Reference 1: Ichiro Kirikae, Otorhinolaryngology;
Non-patent Reference 2: Atsushi Komathuzaki, Client 21;
Non-patent Reference 3: Angelborg, C. et al.: Hyperosmotic solutions and hearing in Meniere's disease. Am. J. Otol. 3: 200-2 (1982);
Non-patent Reference 4: Takeda, T. et al.: The rebound phenomenon of glycerol-induced changes in the endolymphatic space. Acta Otolaryngol. 119: 341-4 (1999);
Non-patent Reference 5: Matsubara, H. et al.: Rebound phenomenon in glycerol test. Acta Otolaryngol. Suppl. 419: 115-22 (1984);
Non-patent Reference 6: Sawada, S. et al.: Aquaporin-1 (AQP1) is expressed in the stria vascularis of rat cochlea. Hear. Res. 181:15-9 (2003);
Non-patent Reference 7: Sawada, S. et al.: Aquaporin-2 regulation by vasopressin in the rat inner ear. Neuroreport. 13: 1127-9 (2002);
Non-patent Reference 8: Takeda, T. et al.: The effects of V2 antagonist (OPC-31260) on endolymphatic hydrops. Hear. Res. 183: 9-18 (2003);
Non-patent Reference 9: Takeda, T. et al.: Antidiuretic hormone (ADH) and endolymphatic hydrops. Acta Otolaryngol. Suppl. 519: 219-22 (1995);
Non-patent Reference 10: Takeda, T. et al.: Endolymphatic hydrops induced by chronic administration of vasopressin. Hear. Res. 140:1-6 (2000);
Non-patent Reference 11: Safwate A. et al.: Renin-aldosterone system and arginine vasopressin in diarrhoeic calves. Br. Vet. J. 147:533-7 (1991);
Non-patent Reference 12: Kakigi, A. et al.: Time course of dehydratic effects of isosorbide on experimentally induced endolymphatic hydrops in guinea pigs. ORL J. Otorhinolaryngol. Relat. Spec. 66:291-296 (2004).

SUMMARY OF THE INVENTION

Problem to be Solved

As described above, conventional pharmaceutical compositions for the treatment of Meniere's disease comprising saccharides or sugar alcohols as an active ingredient take a long period of time to exert the decompression effect or are apt to produce a vicious rebound phenomenon. Also, in the therapy, the compositions are orally administered in large amounts (e.g. 20-30 g as a single dose) at three times per day for about two weeks, and therefore the characteristic evacuant action and non-transient diarrhea are more or less developed. As the result, the dehydration is easily developed secondarily, and resulting in elevating the plasma AVP level inevitably. In order to ensure exertion of the therapeutic effect, it is thus necessary to suppress the elevation of the plasma AVP level, for example, by incorporating with antidiarrheal drugs. It is hardly expected that the gastrointestinal symptoms caused by saccharides or sugar alcohols would improves by the use of conventional antidiarrheal drugs or anti-flatulents, because these cathartic symptoms are quite peculiar. Namely, in spite that the patients who are not constipated and do not basically need as laxatives, they have to take saccharides or sugar alcohols in high amounts continuously for the other purpose except for the treatment for diarrhea. Thus they are placed not under the contradicted condition, in which they have to take saccharides or sugar alcohols as laxatives while inhibiting the diarrhea.

In addition to diarrhea, flatulence, distension and borborygmus are known as the side-effects along with the high dose. Without wishing to be limited by the mechanisms of actions, those side-effects seem to be produced by making the administered saccharides transported from the small intestine to the large intestine in their undigested forms, making them fermented by bacteria in the large intestine to form short-chain fatty acids such as butyric acid and propionic acid and stimulating the intestinal mucosa with said short-chain fatty acids to enhance the peristaltic action. Also, the intestinal gas such as carbon dioxide, hydrogen and methane is produced from saccharides themselves at the same time. Therefore, those noxious conditions cannot be treated by conventional anti-flatulents, as stated above.

In addition, the effective substances are required to be administered in large amounts, and easiness of administration and convenience for carrying are also desired.

Accordingly, the problem to be solved by the present invention is to provide a pharmaceutical composition for treating Meniere's disease with no or little noxious gastrointestinal symptoms such as a cathartic effect, further with easiness in intake and carrying, in particular further with rapid exertion of the effect, which comprises saccharides or sugar alcohols as the active ingredients.

Means to Solve the Problem

As an extensive study for solving the above problem, it has now been found that the undesired gastrointestinal symptoms such as a cathartic effect can be eliminated by incorporating monosaccharides or oligosaccharides, or sugar alcohols thereof with polysaccharides in a certain range of amounts. It has also been found that both of the volume and weight of the composition are significantly reduced, for example, to approximately half by formulating such composition in a gel, powder or granule form. The present invention is based on these findings.

In one embodiment, the present invention provides a pharmaceutical composition for treating Meniere's disease, which comprises (a) at least one of monosaccharides and oligosaccharides, and sugar alcohols thereof; and (b) at least one of polysaccharides, the weight ratio of the components (a):(b) being from about 100:2 to about 100:50.

In another embodiment, the present invention provides a pharmaceutical composition for treating Meniere's disease in a gel form, which comprises (a) at least one of monosaccharides and oligosaccharides, and sugar alcohols thereof; and (b) at least one of polysaccharides; the weight ratio of the components (a):(b) being from about 100:2 to about 100:50.

In a further embodiment, the present invention provides a method for manufacturing a gel preparation, which comprises adding about 10 to 55 parts by weight of water to 100 parts by weight of (a) at least one of monosaccharides and oligosaccharides, and sugar alcohols thereof and (b) at least one of polysaccharides and mixing them, the weight ratio of the components (a):(b) being from about 100:2 to about 100:50.

In yet a further embodiment, the present invention provides the use of (a) at least one of monosaccharides and oligosaccharides, and sugar alcohols thereof and (b) at least one of polysaccharides in a certain weight ratio, i.e. the weight ratio of the components (a):(b) being from about 100:2 to about 100:50, for the manufacture of a pharmaceutical composition for treating Meniere's disease.

In still a further embodiment, the present invention provides a method for treating Meniere's disease, which comprises administering to a patient suffering from Meniere's disease a pharmaceutically effective amount of the pharmaceutical composition as defined above.

Effect of the Invention

The pharmaceutical composition of the present invention for treating Meniere's disease comprises monosaccharides and oligosaccharides, and sugar alcohols thereof (hereinafter referred to as "saccharides and/or sugar alcohols") with polysaccharides in certain ranges of amounts, thereby the side effect caused by saccharides and/or sugar alcohols including digestive disorders such as diarrhea as the major complaint such as diarrhea being eliminated or reduced and decompression effect on endolymphatic hydrops as the target for treatment of Meniere's disease being achieved surely and successfully. In addition, the rebound phenomenon can be reduced or inhibited, and also the time for exhibition of the therapeutic effect can be shortened in comparison with the sole administration of saccharides and/or sugar alcohols.

In another embodiment, the composition may be formulated in a gel form to reduce the volume. Therefore, such composition is convenient for storage, carrying and dosing. In addition, the gel formulation may be prepared in powder, granule or the like by a conventional procedure such as drying, grinding and granulating for convenience on storage, carrying and dosing. The dried formulation such as powder, granule or the like may be changed immediately to a gel (gelatinous) easily taken by adding a small amount of water thereto on the administration.

DETAILED DESCRIPTION OF THE PREFERRED EMBODIMENTS

Figure 1:
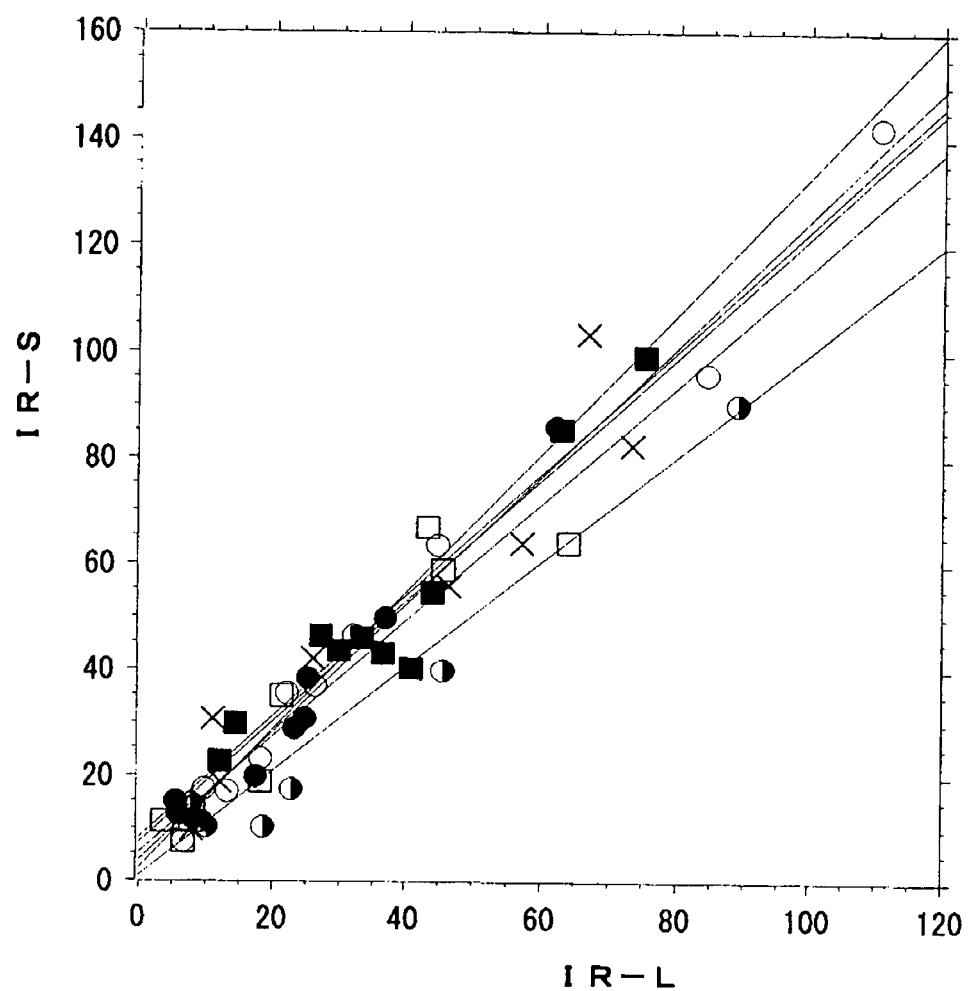
FIG. 1 shows scattergram and regression lines of the increase ratio of the length of Reissner's membrane (IR-L) and the increase ratio of the cross-sectional area of the scala media (IR-S) of the operated ears of Group 1 in Example 2; the sequential changes of the decompression effect after the administration of erythritol

The pharmaceutical composition of the present invention for treating Meniere's disease comprises essentially (a) at least one selected from monosaccharides and oligosaccharides, and sugar alcohols thereof; and (b) at least one selected from polysaccharides in a certain proportion.

In this specification, the terms "monosaccharide", "oligosaccharide", "polysaccharide" and "sugar alcohol" as used hereinbefore and hereinafter mean as commonly understood in the art field, respectively [cf. Kirk-Othmer: Encyclopedia of Chemical Technology, 4th Ed., Vol. 4, page 912 (1992); "Encyclopedia CHEMICA", compact edition, Kyoritsu Shuppan, Volume 4, page 807, Volume 5, pages 662 and 762, Volume 6, pages 306, 308 and 369 (1984), etc.]. For example, the terms "monosaccharide", "oligosaccharide" and "polysaccharide" may respectively mean carbohydrates as molecules which are not further degraded through hydrolysis, carbohydrates which may be degraded to small definite numbers (e.g. 2 to 10) of monosaccharide molecules through hydrolysis, and carbohydrates which may be degraded to large indefinite numbers (e.g. at least 35) of monosaccharide molecules through hydrolysis. Oligosaccharides are preferred to be disaccharides. The term "sugar alcohol" may mean polyhydric alcohols corresponding to saccharides in which the aldehyde groups and the ketone groups are reduced respectively to primary alcohol groups and secondary alcohol groups.

Within the context of the present invention, preferred monosaccharides, oligosaccharides and sugar alcohols thereof as the component (a) include, but not limited to, glycerol, erythritol, xylitol, xylose, sorbitol, isosorbitol, maltitol, lactitol, mannitol, etc. and particularly erythritol, xylitol and isosorbitol. Preferred polysaccharides as the component (b) include, but not limited to, pectin, xanthan gum, guar gum, gum arabic, locust bean gum, Tara gum, sodium alginate, sodium carboxymethyl cellulose, hydroxypropyl cellulose, agar, carrageenan, etc., particularly pectin, xanthan gum, sodium alginate and sodium carboxymethyl cellulose. In each case, one or more of them may be used.

The proportion (weight ratio) of the component (a) such as monosaccharides, oligosaccharides and/or sugar alcohols thereof and the component (b) such as polysaccharides may be about 100:2-50, preferably about 100:5-50, more preferably about 100:10-40. When the proportion is out of said range, the anti-diarrhea effect of polysaccharides will be not fully exhibited.

By adding purified water to the components (a) and (b) in an amount of about 10 to 55% by weight, preferably about 15 to 50% by weight, based on the total amount of the components (a) and (b) and mixing at an ambient temperature or, if necessary, at an elevated temperature, there is obtained a uniform mixture gelled to jelly. When the amount of purified water is smaller than about 10% by weight, the mixture will give an unfavorably increased viscosity. When the amount is larger than about 55% by weight, the mixture will not give a gel of favorable quality due to excessive dilution.

The gel formulation may be dried and ground to provide a powder. Alternatively, said mixture may be granulated, for example, by extrusion granulating process, dried and pelletized to provide granules.

Drying, grinding and granulating processes may be accomplished by any conventional procedures.

If required, the composition of the present invention may be incorporated with one or more of pharmaceutically acceptable carriers, excipients, diluents, binders, antiseptics, stabilizers, flavoring agents, coloring agents, etc. in addition to said active ingredients.

Provided that the purpose of the present invention is not deteriorated, the pharmaceutical composition of the invention may be incorporated with one or more of any medicaments other than saccharides and sugar alcohols. Such medicaments include, but not limited to, antacidic and/or intestinal regulating agents such as dried aluminum hydroxide gel, natural aluminum silicate and precipitated calcium carbonate, agents for improving circulation in the ear such as β-adrenergic nerve inhibitors, vasodilative agents and brain circulation improving agents, agents for ameliorating labyrinthine hydrops such as diuretics, agents for sedation or anti-emesis such as sedatives or autonomic agents, etc.

The therapeutically effective amounts of saccharides or sugar alcohols may vary depending on various factors such as the pathology of diseases to be treated, the age, sex and general health of the subject to be treated, etc. In general, satisfactory results are obtained at a daily dosage of from about 0.5 to 3.0 g/kg, preferably from about 0.8 to 1.5 g/kg, divided into one to several times (e.g. three times).

The pharmaceutical composition for treating Meniere's disease according to the present invention may be administered in a gel form as such, which is formed by mixing saccharides or sugar alcohols with polysaccharides, or in a powder or a granule form prepared from the gel in a conventional manner.

The volume of the powder or granule formulation obtained from the gel is significantly reduced, for example, by about 50%, preferably by about 60% or more, in comparison with the volume of saccharides or sugar alcohols themselves. Therefore, said formulation is convenient for storage or carrying and easy for administration.

Alternatively, the powder or granule formulation may be admixed with water in an amount of about 10 to 55% by weight on the use for gelatin to give jelly, which is more easily administered.

The gel formulation of the present invention can be conveniently administered in comparison with any conventional liquid formulation such as a saturated aqueous solution of saccharides or sugar alcohols, because the volume of said gel formulation is so significantly reduced to about one-third of that of the liquid formulation.

The present invention is illustrated by Examples and Reference Examples as shown below, which never constitute any limitation of the present invention. On conducting the animal experiment, we tried not to sacrifice too many animals for laparotomy, because the results may be fully obtained by observing, inspecting and palpating test animals and excreted feces and we made a consideration of public opinion for animal protection. To avoid the effect of multiple administrations, animals administered with saccharides or sugar alcohols are incorporated into the test only once.

The following abbreviations are used in Tables in Examples and Reference Examples below:

Ery: erythritol

IB: isosorbitol

P: pectin

XG: xanthan gum

Al: sodium alginate glycerol

Gly: glycerol

CMC: sodium carboxymethyl cellulose

PVP: polyvinylpyrrolidone

GG: guar gum

AG: gum arabic

The criteria for analyzing the conditions of feces (hardness, shape and spaces of feces in the intestine) are as shown in Table 2:

TABLE 2

Criteria of feces conditions

1) Criteria of hardness and shape

| Stage | Score | Standard for classification |
|---|---|---|
| Muddy | 0 | Muddy or watery, no shape feces |
| Soft | 1 | The shape had already changed, or it could quite easily change by pushed with fingers. |
| Slightly soft | 2 | The shape could rather easily change by pushed with fingers. |
| Normal | 3 | The feces were as hard as those of animals fed normal diet at least for 3 days. |

TABLE 2-continued

| Criteria of feces conditions | | |
|---|---|---|
| Hard | 4 | Harder than normal. The shape could rarely change by pushied with fingers. |

| 2) Criteria for spaces of feces | |
|---|---|
| Criteria | |
| Muddy | The intestine is uniformly filled with muddy feces. |
| Extraordinary irregular | The shapes of feces are formed. Their spaces are spread within from 0.5 to 10 cm. |
| Irregular | The almost normal feces are formed. Their spaces are spread within from 0.5 to 4 cm. |
| Regular | The spaces of feces are regularly spread within about 1 cm. |

The hardness and microscopic findings of feces from the group administered with distilled water were assessed as "Normal" scoring 3, the feces having normal shape and the shape could rather easily change by pushing with fingers were assessed as "Slightly soft" scoring 2, those of which the shape had already changed or it could quite easily change by pushed with fingers were assessed as "Soft" scoring 1, and those of which the shape is muddy or watery or of no shape were assessed "Muddy" scoring 0. To be precese, there are no watery feces because of the nature of diets and thus the muddy feces correspond to watery and muddy feces in human.

As the results of the laparotomy, in case only 2 to 3 cm of feces are formed in the rectum, some animals extrude soft-like feces and assessed as successfully inhibited the diarrhea, although the intestine is filled with muddy feces without a shape. Since the muddy feces comprise large content of water, they induce the high abdominal pressure and the flatulence and distension. In some animals in which the feces are formed in the intestine, the generation of gas was observed in the space of feces by paracentesis during laparotomy. In the case of gas generation, it appears that noxious symptom such as the flatulence and distension are synergistically deteriorated. Therefore, we assessed not only based on the hardness of feces, but also the size, smoothness of the surface and amount of feces.

EXAMPLE 1

In these experiments, I observed is the diarrhea caused by saccharides or sugar alcohols and antidiarrheal effect of saccharides. Guinea pigs orally received saccharides or sugar alcohols, for example tetrose such as erythritol, pentose such as xylitol or xylose, hexose such as isosorbitol or the like in combination with or without polysaccharides for observation of the feces up to 6 hours after the administration.

Subjects and Methods:

Guinea pigs (body weight 280 to 320 g, normal feces) were divided into four groups: for Group 1-a, xylitol alone (Reference Example 1), or xylitol and xanthan gum or pectin; for Group 1-b, xylose alone (Reference Example 2), xylose and xanthan gum or pectin; for Group 1-c, erythritol alone (Reference Example 3), erythritol and pectin, erythritol and xanthan gum, or erythritol, pectin and natural aluminum silicate gel or calcium carbonate; and for Group 1-d, isosorbitol alone (Reference Example 4), or isosorbitol and xanthan gum or pectin were orally administered, respectively. The amount of saccharides or sugar alcohols and polysaccharides to be administered are as shown in Tables 3, 4 and 5. The compounds are dissolved in distilled water and 8 ml/kg of said solution were administered as a single dose.

The feces were observed during 6 hours after the administration. When the animals fell into the most serious condition, the hardness and shape of the feces from said animals were assessed as the effect by saccharides or sugar alcohols in the animals. The results are as shown in Tables 3, 4 and 5.

TABLE 3

Antidiarrheal effect of polysaccharides on pentose

| Active agent | Dosage | Additives XG or P | | Number of animals | Hardness of feces | | | |
|---|---|---|---|---|---|---|---|---|
| | | | | | Normal | Slightly soft | Soft | Muddy |
| 1-a | | | | | | | | |
| Xylitol | 0 g/kg | — | — | 5 | 5 | 0 | 0 | 0 |
| Xylitol | 1.4 g/kg | — | — | 5 | 5 | 0 | 0 | 0 |
| Xylitol | 2.1 g/kg | — | — | 5 | 4 | 1 | 0 | 0 |
| Xylitol | 2.8 g/kg | — | — | 5 | 0 | 1 | 1 | 3 |
| Xylitol | 2.8 g/kg | XG | 0.12 g/kg | 5 | 0 | 2 | 2 | 1 |
| Xylitol | 2.8 g/kg | XG | 0.2 g/kg | 5 | 3 | 0 | 1 | 1 |
| Xylitol | 2.8 g/kg | XG | 0.3 g/kg | 5 | 5 | 0 | 0 | 0 |
| Xylitol | 2.8 g/kg | P | 0.25 g/kg | 5 | 0 | 2 | 2 | 1 |
| Xylitol | 2.8 g/kg | P | 0.35 g/kg | 5 | 5 | 0 | 0 | 0 |
| 1-b | | | | | | | | |
| Xylose | 2.8 g/kg | — | — | 5 | 0 | 1 | 3 | 1 |
| Xylose | | XG | 0.2 g/kg | 6 | 5 | 1 | 0 | 0 |
| Xylose | | P | 0.3 g/kg | 5 | 5 | 0 | 0 | 0 |

TABLE 4

Antidiarrheal effect of polysaccharides on tetrose

| Active agent | Dosage | Additives XG or P | | A | C | Number of animals 1-c | Hard | Normal | Slightly soft | Soft | Muddy |
|---|---|---|---|---|---|---|---|---|---|---|---|
| Erythritol | 2.8 g/kg | — | — | — | — | 5 | 0 | 0 | 0 | 0 | 5 |
| Erythritol | 2.8 g/kg | P | 0.1 g/kg | — | — | 5 | 0 | 0 | 0 | 1 | 4 |
| Erythritol | 2.8 g/kg | P | 0.3 g/kg | — | — | 5 | 0 | 0 | 2 | 3 | 0 |
| Erythritol | 2.8 g/kg | P | 0.5 g/kg | — | — | 5 | 0 | 3 | 2 | 0 | 0 |
| Erythritol | 2.8 g/kg | P | 1.0 g/kg | — | — | 5 | 0 | 5 | 0 | 0 | 0 |
| Erythritol | 2.8 g/kg | P | 1.5 g/kg | — | — | 5 | 5 | 0 | 0 | 0 | 0 |
| Erythritol | 2.8 g/kg | P | 0.5 g/kg | A1 | — | 5 | 0 | 4 | 1 | 0 | 0 |
| Erythritol | 2.8 g/kg | P | 0.5 g/kg | A1 | C1 | 5 | 0 | 4 | 1 | 0 | 0 |
| Erythritol | 2.8 g/kg | XG | 0.05 g/kg | — | — | 5 | 0 | 0 | 0 | 1 | 4 |
| Erythritol | 2.8 g/kg | XG | 0.10 g/kg | — | — | 5 | 0 | 2 | 3 | 0 | 0 |
| Erythritol | 2.8 g/kg | XG | 0.15 g/kg | — | — | 5 | 0 | 4 | 1 | 0 | 0 |
| Erythritol | 2.8 g/kg | — | — | A1 | — | 5 | 0 | 0 | 0 | 1 | 4 |
| Erythritol | 2.8 g/kg | — | — | A2 | — | 5 | 0 | 0 | 1 | 1 | 3 |
| Erythritol | 2.8 g/kg | — | — | A3 | C1 | 5 | 0 | 1 | 0 | 1 | 3 |
| Erythritol | 2.8 g/kg | — | — | A3 | C2 | 5 | 0 | 1 | 0 | 1 | 3 |

A1: natural aluminum silicate 0.17 g/kg
A2: natural aluminum silicate 0.35 g/kg
A3: natural aluminum silicate 0.7 g/kg
C1: calcium carbonate 50 mg/kg
C2: calcium carbonate 100 mg/kg

TABLE 5

Antidiarrheal effect of polysaccharides on hexose

| Saccharide or sugar alcohol | Dosage | Additives | | Number of animals 1-d | Normal | Slightly soft | soft | Muddy |
|---|---|---|---|---|---|---|---|---|
| Isosorbitol | 1.4 g/kg | — | | 4 | 3 | 1 | 0 | 0 |
| Isosorbitol | 2.1 g/kg | — | | 4 | 0 | 2 | 2 | 0 |
| Isosorbitol | 2.8 g/kg | — | | 7 | 2 | 2 | 2 | 1 |
| Isosorbitol | 2.8 g/kg | XG | 0.05 g/kg | 7 | 5 | 2 | 0 | 0 |
| Isosorbitol | 2.8 g/kg | XG | 0.15 g/kg | 7 | 7 | 0 | 0 | 0 |
| Isosorbitol | 2.8 g/kg | P | 0.15 g/kg | 7 | 6 | 1 | 0 | 0 |
| Isosorbitol | 2.8 g/kg | P | 0.3 g/kg | 7 | 7 | 0 | 0 | 0 |
| Isosorbitol | 3.5 g/kg | — | | 4 | 0 | 0 | 1 | 3 |
| Isosorbitol | 3.5 g/kg | P | 0.3 g/kg | 4 | 4 | 0 | 0 | 0 |
| Isosorbitol | 3.5 g/kg | XG | 0.2 g/kg | 4 | 4 | 0 | 0 | 0 |
| Isosorbitol | 5.6 g/kg | — | | 3 | 0 | 0 | 0 | 3 |
| Isosorbitol | 5.6 g/kg | P | 0.3 g/kg | 3 | 3 | 0 | 0 | 0 |

TABLE 6

Antidiarrheal effect of polysaccharides on disaccharides

| Active agent | Dosage | Additives XG or GG | | Number of animals 1-e | Hard | Normal | Slightly soft | Soft | Muddy |
|---|---|---|---|---|---|---|---|---|---|
| Maltitol | 2.8 g/kg | — | — | 6 | 0 | 0 | 0 | 0 | 6 |
| Maltitol | 2.8 g/kg | XG | 0.07 g/kg | 4 | 0 | 0 | 0 | 0 | 4 |
| Maltitol | 2.8 g/kg | XG | 0.14 g/kg | 4 | 0 | 0 | 0 | 1 | 3 |
| Maltitol | 2.8 g/kg | XG | 0.28 g/kg | 4 | 0 | 0 | 2 | 1 | 1 |
| Maltitol | 2.8 g/kg | XG | 0.56 g/kg | 4 | 0 | 2 | 2 | 0 | 0 |
| Maltitol | 2.8 g/kg | XG | 1.12 g/kg | 4 | 0 | 2 | 2 | 0 | 0 |
| Maltitol | 2.8 g/kg | GG | 0.28 g/kg | 4 | 0 | 0 | 0 | 0 | 4 |
| Maltitol | 2.8 g/kg | GG | 0.56 g/kg | 4 | 0 | 1 | 1 | 2 | 0 |
| Maltitol | 2.8 g/kg | GG | 1.12 g/kg | 4 | 0 | 2 | 2 | 0 | 0 |

The results from Example 1 are as shown below.

1-a) Xylitol

Forty five guinea pigs excreting normal feces were divided into 9 groups wherein each group comprises 5 animals, and then were orally administered xylitol solution as shown in Table 3.

a) Effect of Dose of Xylitol (Reference Example 1)

No diarrhea was shown in the group administered with 1.4 g/kg of xylitol. In the group administered with 2.1 g/kg of xylitol, one animal had soft feces 3 hours after, which may easily change its shape by pushing with fingers. In the group administered with 2.8 g/kg, while no disorder was shown in all animals 1 hour after, all animals had more or less clear diarrhea 2 hours after. Three to four hours after the administration, the abdominal symptom became the most serious, and more than half of animals had muddy feces, while their feces returned to almost normal 6 hours after.

b) Xylitol Added Xanthan Gum 2.8 g/kg of xylitol added each one of 0.12 g/kg, 0.2 g/kg or 0.3 g/kg of xanthan gum were orally administered. While no disorder was shown in all animals up to 2 hours after, the disorder was developed 3 to 4 hours after. The assessment of the feces at the times is shown in Table 3. The normal feces had been increasing as more xanthan gum was administered. In the group administered with xylitol added 0.3 g/kg of xanthan gum, no soft feces were shown during the test period.

c) Xylitol Added Pectin 2.8 g/kg of xylitol added each one of 0.25 g/kg or 0.35 g/kg of pectin were orally administered. In the group administered with xylitol added 0.2 g/kg of pectin, the feces gradually softened from 2 hours after and its peak had come 3 to 4 hours after. In the group administered with xylitol added 0.3 g/kg of pectin, no soft feces were shown.

1-b) Xylose

Sixteen guinea pigs excreting normal feces were divided into 3 groups as shown in Table 3. In the group administered with 2.8 g/kg of xylose alone, 4 animals out of 5 showed muddy or soft feces. In the group administered with xylose added 0.2 g/kg of xanthan gum or 0.3 g/kg of pectin, no soft feces were shown, except for one animal of slightly soft. The difference of the hardness of feces from those groups are significant in comparison with Reference 2 (both cases, $p<0.01$, Mann-Whitney test). During diarrhea, mild or moderate flatulence and distension, and also slight movement of gas were touched.

1-c) Erythritol

Seventy five guinea pigs excreting normal feces were divided into 15 groups, wherein each group comprises 5 animals, and then were orally administered erythritol solution with or without additives as shown in Table 4.

a) Erythritol 2.8 g/kg Alone (Reference Example 2)

Three hours after muddy feces were shown in all animals and continued up to 6 hours after in 3 animals.

b) Erythritol Added Pectin 2.8 g/kg of erythritol added each one of 0.1 g/kg, 0.3 g/kg, 0.5 g/kg, 1.0 g/kg or 1.5 g/kg of pectin were orally administered. In the group administered with erythritol added 0.5 g/kg of pectin, the feces were normal in more than half of the animals and in the group administered with erythritol added 1.5 g/kg of pectin, the feces were hard rather than normal.

c) Erythritol Added Pectin, Natural Aluminum Silicate, Calcium Carbonate 2.8 g/kg of erythritol, 0.5 g/kg of pectin and 0.17 g/kg of natural aluminum silicate (Adsorbin) or 2.8 g/kg of erythritol, 0.5 g/kg of pectin, 0.17 g/kg of natural aluminum silicate and 50 mg/kg of calcium carbonate were administered to animals. In both groups, the feces from almost all animals were normal as shown in Table 4.

The difference is not significant in comparison with the group administered with erythritol alone, suggesting that no preferred synergistic effect is produced by adding conventional antiflatulent (Mann-Whitney test).

d) Erythritol Added Xanthan Gum 2.8 g/kg of erythritol added 0.05 g/kg of xanthan gum did not show any antidiarrheal effect. Meanwhile, in the group administered with erythritol added 0.1 g/kg of xanthan gum, no soft feces was shown and in the group administered with erythritol added 0.15 g/kg of xanthan gum, normal feces were shown in 4 animals out of 5 owing to the significant antidiarrheal effect (each cases, $p<0.01$, Mann-Whitney test).

e) Erythritol Added Natural Aluminum Silicate and Calcium Carbonate

In the groups administered with 2.8 mg/kg of erythritol added each one of 0.17 g/kg, 0.35 g/kg or 0.7 g/kg of natural aluminum silicate (Adsorbin) and/or 50 mg/kg or 100 mg/kg of calcium carbonate, no significant antidiarrheal effect was shown as shown in Table 4 (Mann-Whitney test).

1-d) Isosorbitol

Sixty one guinea pigs excreting normal feces were divided into 12 groups, and then were orally administered aqueous Isosorbitol solution alone or isosorbitol added xanthan gum or pectin as shown in Table 5.

a) Effect of Dose of Isosorbitol when Isosorbitol is Administered Alone (Reference Example 4)

In the group administered with 1.4 g/kg of isosorbitol, slightly soft feces were shown in only 1 animal. In the group administered with 2.1 g/kg of isosorbitol, 3 hours after the administration soft feces were shown in 2 animals and slightly soft feces were shown in 2 animals. In the group administered with 2.8 g/kg of isosorbitol, while no disorder was shown 1 hour after, most animals started to have diarrhea 2 hours after. Three to four hours after the symptom became most serious, while 6 hours after they recovered to almost normal.

b) Isosorbitol Added Xanthan Gum 2.8 g/kg of isosorbitol added each one of 0.05 g/kg (1.8% by weight) or 0.15 g/kg (5.4% by weight) of xanthan gum were orally administered. While no disorder was shown in all animals up to 2 hours after the administration, to 4 hours after the diarrhea was developed. The assessment of the feces at the time is shown in Table 5. The more increasing normal feces had been, the more xanthan gum were administered. In the group administered with isosorbitol added 0.15 g/kg of xanthan gum, no soft feces were shown during the examination.

c) Isosorbitol Added Pectin 2.8 g/kg of isosorbitol added each one of 0.15 g/kg or 0.3 g/kg of pectin were orally administered. Almost no diarrhea condition was developed. In the group administered with isosorbitol added 0.15 g/kg of pectin, no soft feces were shown. In the group administered with isosorbitol added 0.3 g/kg of pectin, normal feces were shown in all animals.

1-e) Maltitol

Thirty eight guinea pigs excreting normal feces were divided into 9 groups, and then were orally administered maltitol solution with or without additives such as xanthan gum or guar gum as shown in Table 6.

a) Maltitol Alone

When 2.8 g/kg of maltitol, disaccharides, was administered, muddy feces were shown in all animals.

When monosaccharides or alcohol thereof was administered, the peak of diarrhea came 3 hours after the administration. The development of diarrhea by the administration of maltitol was relatively slower than those by monosaccharides or alcohol thereof. Namely, when maltitol was administered, 3 hours after the administration the feces started to soften, 4 hours after soft feces were shown in all animals and among those muddy feces were shown in 5 animals. The muddy feces were shown in all animals 5 hours after and lasted till 12 hours after. Eighteen hours after it started on a gradual recovery trend and 24 hours after or later, normal feces were shown in half of the animals.

Five hours after or later, the animals suffered by pushing their abdomen and passed gas. The abdominal distension was observed on inspections.

b) Maltitol Added Xanthan Gum 2.8 mg/kg of maltitol added each one of 0.07 g/kg, 0.14 g/kg, 0.28 g/kg, 0.56 g/kg or 1.12 g/kg of xanthan gum were orally administered.

In the group administered with maltitol added 0.07 g/kg of xanthan gum, the diarrhea was rarely inhibited by polysaccharides. In the group administered with maltitol added 0.14 g/kg of xanthan gum, the feces were started to soften 3 hours after and the condition was exacerbated. 5 hours after, muddy feces were shown in 2 animals and soft feces were shown in the remaining 2 animals. The same condition was also observed 12 hours after. Eighteen hours after it started on a gradual recovery trend and 24 hours after or later, normal feces were shown in all animals. The anti-diarrhea effect of xanthan gum was not shown (no significant difference, (Mann-Whitney test).

In the group administered with maltitol added 0.28 g/kg of xanthan gum, the feces were started to soften 3 hours after and no normal feces was shown in all animals 6 hours after, as being similar to the group administered with maltitol added 0.14 g/kg of xanthan gum. Among them, soft feces were shown in one animal. The normal feces were shown in half of the animals 12 hours after and all animals recovered 24 hours after. The anti-diarrhea effect by xanthan gum was not sufficient.

In both groups, the animals suffered. The abdominal distension was found by inspections and the generation of gas was found by palpations.

In the both groups administered with maltitol added 0.56 g/kg (20% by weight) and 1.12 g/kg (40% by weight) of xanthan gum, slightly soft feces were shown in half of the animals between 6 hours and 18 hours after the administration and the hardness of feces were recovered in all animals 24 hours after. The antidiarrheal effect by the addition of xanthan gum was shown (in both groups, p<0.05, Mann-Whitney test). On the other hand, the amount of feces was remarkably reduced 5 hours after or later. The amount was reduced to less than one-third compared with normal condition between 9 hours and 15 hours after.

c) Maltitol Added Guar Gum (GG)

2.8 mg/kg of maltitol added 0.28 g/kg, 0.56 g/kg or 1.12 g/kg of GG were orally administered.

In the group administered with maltitol added 0.28 g/kg (10% by weight) of GG, soft feces were shown in some animals 2 hours after. Four hours after, soft feces were shown in one animal and muddy feces were shown in the others. Muddy feces were shown in all animals between 5 hours and 12 hours after. Eighteen hours after, soft feces were shown in 4 animals and they recovered 24 hours after. The antidiarrheal effect of GG was less than that of XG. The abdominal distension was found by inspections. The generation and the movement of gas were recognized by palpations.

In the group administered with maltitol added 0.56 g/kg (20% by weight) of GG, soft feces were shown in some animals 3 hours after. Five to 6 hours after, normal, slightly soft and soft feces were shown in one animal, respectively. It was the peak of diarrhea. In the other animals than one of normal feces, the shape of feces is smaller and more irregular than that of normal other than one. The amount of feces was reduced to about half. The abdominal distension was found by inspections. The generation and the movement of gas were recognized by palpations. The antidiarrheal effect of GG was less than that of same amount of XG. The amount of feces was more than that of XG to some extent (half of normal condition) and also the abdominal distension was less.

In the group administered with maltitol added 1.12 g/kg (40% by weight) of GG, 3 hours after or later the amount of feces was less and its shape was small and irregular. Slightly soft feces were shown in half of the animals between 5 hours and 18 hours after. Twenty four hours after, all animals recovered in their hardness of feces. The antidiarrheal effect of xanthan gum was shown (in both groups, p<0.05, Mann-Whitney test). The gastrointestinal symptom became more severe depending on the amount of GG. The generation of gas was recognized by palpations and the movement of gas in the intestine was touched and heard by pushing weakly with fingers. On pushing the abdomen strongly, the animal squeaked and suffered. The antidiarrheal effect of GG was less than that of the same amount of XG. The amount of feces was more than XG, i.e. about half of the normal. Although the abdominal distension was similar, the animals suffered less.

The difference between monosaccharides and disaccharides such as maltitol is that the development of diarrhea is later than that by monosaccharides, i.e. is 4 to 5 hours after or later, that the peak continues for about 12 hours, as well as the severe abnormal fermentation is developed in the intestine during those periods. The administration of relatively large amount of xanthan gum or guar gum may inhibit diarrhea, however the progression of the condition is different from that of monosaccharides, for example abnormal fermentation is developed in the intestine. The time course of the hardness of feces is shown in Table 7 (average of 4 animals).

TABLE 7

Time-cource of the hardness of feces after the administration

| Sugar alcohol | Additives | | Hours after the administration (hr) | | | | | | | | |
|---|---|---|---|---|---|---|---|---|---|---|---|
| Maltitol | XG or GG | | 1 | 2 | 3 | 4 | 5 | 6 | 12 | 18 | 24 |
| 2.8 g/kg | — | — | 3 | 2.3 | 1.7 | 0.2 | 0 | 0 | 0 | 1.2 | 2.5 |
| 2.8 g/kg | XG | 0.07 g/kg | 3 | 3 | 0.5 | 0 | 0 | 0 | 0 | 1 | 2.5 |
| 2.8 g/kg | XG | 0.14 g/kg | 3 | 3 | 2.5 | 1.5 | 0.5 | 0.5 | 0.5 | 2 | 3 |
| 2.8 g/kg | XG | 0.28 g/kg | 3 | 3 | 2.5 | 2.5 | 1.5 | 1.8 | 2.5 | 2.8 | 3 |
| 2.8 g/kg | XG | 0.56 g/kg | 3 | 3 | 3 | 3 | 3 | 2.5 | 2.5 | 2.5 | 3 |
| 2.8 g/kg | XG | 1.12 g/kg | 3 | 3 | 3 | 3 | 3 | 2.5 | 2.5 | 2.5 | 3 |
| 2.8 g/kg | GG | 0.28 g/kg | 3 | 2.3 | 1.7 | 0.2 | 0 | 0 | 0 | 1.2 | 2.5 |
| 2.8 g/kg | GG | 0.56 g/kg | 3 | 3 | 2.8 | 2.3 | 1.8 | 1.8 | 2.8 | 2.8 | 3 |
| 2.8 g/kg | GG | 1.12 g/kg | 3 | 3 | 3 | 3 | 2.5 | 2.5 | 2.5 | 2.5 | 3 |

In addition, the antidiarrheal effect of polysaccharides on the diarrhea caused by other saccharides or sugar alcohols was examined.

[Mannitol and Sodium Carboxymethyl Cellulose]

Eight guinea pigs excreting normal feces were divided into 2 groups, and then were administered as shown below. Feces were observed for 6 hours after the administration. The result is shown in Table 8.

TABLE 8

Mannitol and CMC

| Saccharide or sugar alcohol | Dosage | Additives | | Number of animals | Hardness of feces 3 | 2 | 1 | 0 |
|---|---|---|---|---|---|---|---|---|
| mannitol | 2.8 g/kg | — | | 4 | 0 | 1 | 2 | 1 |
| mannitol | 2.8 g/kg | CMC | 0.2 g/kg | 4 | 2 | 2 | 0 | 0 |

Diarrhea caused by mannitol was significantly ameliorated by administering with mannitol added about 7.1% by weight of CMC ($p<0.05$, Mann-Whitney test). No abdominal distension was found on both inspections and palpations, suggesting mild gastrointestinal symptoms.

[Sorbitol and Hydroxypropyl Cellulose]

Ten guinea pigs excreting normal feces were divided into 2 groups, and then were administered as shown below. Feces were observed for 6 hours after the administration. The result is shown in Table 9.

TABLE 9

Sorbitol and HPC (+CMC)

| Saccharide or sugar alcohol | Dosage | Additives | | Number of animals | Hardness of feces 3 | 2 | 1 | 0 |
|---|---|---|---|---|---|---|---|---|
| Sorbitol | 2.8 g/kg | — | | 5 | 0 | 1 | 2 | 2 |
| Sorbitol | 2.8 g/kg | HPC | 0.15 g/kg | 5 | 2 | 3 | 0 | 0 |

0.05 g/kg of CMC (sodium carboxymethyl cellulose) was added to HPC and suspended.

Diarrhea caused by sorbitol was significantly ameliorated by the addition of about 5.4% by weight of HPC (suspended in about 0.18% by weight of sodium carboxymethyl cellulose) ($p<0.05$, Mann-Whitney test). No abdominal distension was found on both inspections and palpations, suggesting mild gastrointestinal symptom.

[Sorbitol and Guar Gum (Sigma)]

Ten guinea pigs excreting normal feces were divided into 2 groups, and then were administered as shown below. Feces were observed for 6 hours after the administration. The result is shown in Table 10.

TABLE 10

Sorbitol and guar gum

| Saccharide or sugar alcohol | Dosage | Additives | | Number of animals | Hardness of feces 3 | 2 | 1 | 0 |
|---|---|---|---|---|---|---|---|---|
| Sorbitol | 2.8 g/kg | — | | 5 | 0 | 0 | 2 | 3 |
| Sorbitol | 2.8 g/kg | GG | 0.28 g/kg | 5 | 2 | 2 | 1 | 0 |

When sorbitol added 10% by weight of guar gum is administered, normal feces were shown in 2 animals and slightly soft feces were shown in 2 animals. The result shows that the addition of 10% by weight of guar gum to sorbitol may inhibit diarrhea caused by sorbitol ($p<0.05$, Mann-Whitney test). However, 3 to 4 hours after the administration, the amount of feces was reduced to about one-third. Also, mild abdominal distension was recognized by inspections and palpations, as well as the generation and movement of gas was touched by pushing the abdomen with fingers. By pushing the hypogastric region, small feces, whose shape is irregular and amount is less than half of normal feces were gradually extruded.

[Erythritol and Gum Arabic (Sigma)]

Fifteen guinea pigs excreting normal feces were divided into 3 groups, and then were administered as shown below. Feces were observed for 6 hours after the administration. The result is shown in Table 11. It comprises E3H group as a comparative data.

TABLE 11

Erythritol and gum arabic

| Saccharide or sugar alcohol | Dosage | Additives | | Number of animals | Hardness of feces 3 | 2 | 1 | 0 |
|---|---|---|---|---|---|---|---|---|
| Erythritol (E3H group) | 2.8 g/kg | — | | 10 | 0 | 0 | 0 | 10 |
| Erythritol | 2.8 g/kg | AG | 0.28 g/kg | 5 | 0 | 0 | 0 | 5 |
| Erythritol | 2.8 g/kg | AG | 0.56 g/kg | 5 | 0 | 0 | 1 | 4 |
| Erythritol | 2.8 g/kg | AG | 1.12 g/kg | 5 | 0 | 1 | 2 | 2 |

Adding 20% by weight of gum arabic to erythritol could not inhibit diarrhea caused by erythritol (not significant). When erythritol added 40% by weight of gum arabic was administered, diarrhea was ameliorated to some extent ($p<0.05$, Mann-Whitney test), however further secure inhibition of diarrhea should be desirable. In both groups, 3 to 4 hours after the administration the amount of feces were reduced to about one-third. Also, abdominal distension was recognized both by inspections and by palpations, as well as the generation and movement of gas were touched by pushing the abdomen with fingers. By pushing the hypogastric region, small amount of muddy feces was merely extruded and the unpleasant condition was observed.

[Erythritol and Guar Gum (Sigma)]

Fifteen guinea pigs excreting normal feces were divided into 2 groups, and then were administered as shown below. Feces were observed for 6 hours after the administration. The result is shown in Table 12. It comprises E3H group as a comparative test data.

TABLE 12

Erythritol and guar gum

| Saccharide or sugar alcohol | Dosage | Additives | | Number of animals | Hardness of feces 3 | 2 | 1 | 0 |
|---|---|---|---|---|---|---|---|---|
| Erythritol (E3H group) | 2.8 g/kg | — | | 10 | 0 | 0 | 0 | 10 |
| Erythritol | 2.8 g/kg | GG | 0.14 g/kg | 5 | 0 | 0 | 0 | 5 |
| Erythritol | 2.8 g/kg | GG | 0.28 g/kg | 5 | 0 | 0 | 1 | 4 |
| Erythritol | 2.8 g/kg | GG | 0.56 g/kg | 5 | 2 | 2 | 1 | 0 |

When erythritol added 20% by weight of guar gum is administered, normal feces were shown in 2 animals and slightly soft feces were shown in 2 animals. The result shows that the administration of erythritol added 20% by weight of guar gum may inhibit diarrhea ($p<0.01$, Mann-Whitney test). However, 3 to 4 hours after the administration, the amount of feces was reduced to about one-third. Also, abdominal distension was recognized both by inspections and by palpations, as well as the generation and movement of gas were touched by pushing the abdomen by fingers. By pushing the hypogastric region, small feces, whose shape is irregular and amount is less than half of normal feces was gradually extruded and the noxious condition was observed.

The results above shows that diarrhea condition is caused by the oral administration of saccharides or sugar alcohols, that the peak of such diarrhea comes 3 to 4 hours after the administration, however it will recover to some extent 6 hours after or later. Also, it shows that the cathartic effect of saccharides or sugar alcohols may decrease by adding polysaccharides to saccharides or sugar alcohols, and that the antidiarrheal effect may increase depending on the dose of polysaccharides. The inhibiting effect is prone to increase by adding antacids or antiflatulents; however neither clear synergy nor antagonism is shown. The same result was shown in other polysaccharides, such as sodium alginate.

EXAMPLE 2

The endolymphatic hydrops-decompression effect of saccharides or sugar alcohols was evaluated by assaying as below in triplicate. Firstly, guinea pigs received the surgical obliteration of the endolymphatic sac in the left ear to prepare "experimental model animals with endolymphatic hydrops". The surgical obliteration of the endolymphatic sac was carried out by burning the extraskeletal portion in the endolymphatic sac with a bipolar electrocoagulator. An endolymphatic sac plays an important role in the absorption of endolymphatic fluid. The inhibition of absorption of endolymphatic fluid was caused by burning the endolymphatic sac to prepare an experimental endolymphatic hydrops. Those hydrops are progressively formed. The size of hydrops becomes constant 2 weeks to month after the surgery and maintained for several months. In detail, see Non-patent Reference 8 for the surgery.

After 1 month, they were divided into 3 groups: Group 2-1 (groups 1-6), 60 animals; Group 2-2 (groups 7-10), 40 animals; and Group 2-3 (groups 11-20), 66 animals. The animals in Group 2-1 received saccharides or sugar alcohols alone (Reference Example 5). The animals in Group 2-2 orally received saccharides or sugar alcohols added polysaccharides. The animals in Group 2-3 received other combinations of saccharides or sugar alcohols added polysaccharides. Animals were sacrificed after the oral administration and the observation and the assessment the gastrointestinal condition, and observed the morphological change of the cochlea mainly in the operated side (left side), in particular of the endolymphatic hydrops decompression effect.

The laparotomy was carried out to precisely observe abdominal cavity, especially the following two points: 1) the hardness and shape of feces and 2) the length of formed feces, the space between feces and the arrays of feces to estimate cathartic condition, moreover colon, rectus, and intraperitoneal change to estimate noxious abdominal symptom by incision or puncture into the intestinal tract. The results were evaluated according to the criteria described in Table 2. The length of normal feces formed in the rectum and the colon was determined from the anus, and also whether the space of feces is constant was observed.

I were obtained left sides of the temporal bones immediately following fixation and kept them in 10% formalin solution for 10 days or more. They were decalcified with 5% trichloroacetic acid and dehydrated with alcohol in increasing concentration, then embedded in paraffin and celloidin. The prepared blocks were cut serially in the horizontal plane. The mid-modiolar sections were stained in hematoxylin and eosin and studied under a light microscope. For the quantitative assessment of changes of the endolymphatic space, the change ratios of the length of Reissner's membrane and the cross-sectional area of the scala media in each turn were measured from the mid-modiolar sections of the cochlea.

From these parameters, the increase ratios (%) of the length of Reissner's membrane (IR-L) and the cross-sectional area (%) of the scala media (IR-S) of a total of four turns were calculated according to the equation as described below:

Fundamentally, the preparation and the measurement was performed as previously described in Non-patent Reference 8.

The increase ratio of the length of Reissner's membrane $(IR\text{-}L)=100\times\Sigma(Lx-L^*x)/\Sigma L^*x$ (x: first, second, third and fourth turns)

The increase ratio of the cross-section area of the scala media $(IR\text{-}S)=100\times\Sigma(Sx-S^*x)/\Sigma S^*x$ (x: first, second, third and fourth turns)

(1) Group 2-1: Erythritol Alone (Reference Example 4)

Sixty guinea pigs were divided into 6 groups wherein each group includes 10 animals. Those animals received an agent according to Table below. The erythritol aqueous solution was administered at 8 ml/kg as a single dose.

TABLE 13

| Group | Agent | Perfusion (after the administration) |
|---|---|---|
| Group 1: Control | Distilled water 8 ml/kg | 3 hours after |
| Group 2: E1H group | Ery 2.8 g/kg | 1 hour after |
| Group 3: E2H group | Ery 2.8 g/kg | 2 hours after |
| Group 4: E3H group | Ery 2.8 g/kg | 3 hours after |
| Group 5: E6H group | Ery 2.8 g/kg | 6 hours after |
| Group 6: E12H group | Ery 2.8 g/kg | 12 hours after |

A) Gastrointestinal Conditions

The results are shown in Table 14.

TABLE 14

Time-course of feces after the administration of erythritol alone
Group 2-1

| | | Perfusion (hours after) | Length (cm) | Condition of feces | | | | | | | | |
|---|---|---|---|---|---|---|---|---|---|---|---|---|
| | | | | Hardness | | | | | Space | | | |
| | Agent | | | Hard | Normal | Slightly soft | Soft | Muddy | Regular | Irregular | Extraordinary | Muddy |
| Group 1 | Distilled water | 3 | 55.0 ± 8.8 | 0 | 10 | 0 | 0 | 0 | 10 | 0 | 0 | 0 |
| Group 2 | Ery | 1 | 22.8 ± 6.9 | 0 | 10 | 0 | 0 | 0 | 0 | 3 | 7 | 0 |
| Group 3 | Ery | 2 | 1.1 ± 1.4 | 0 | 0 | 0 | 4 | 6 | 0 | 0 | 0 | 10 |
| Group 4 | Ery | 3 | 0 | 0 | 0 | 0 | 0 | 10 | 0 | 0 | 0 | 10 |

TABLE 14-continued

Time-course of feces after the administration of erythritol alone
Group 2-1

| | | Perfusion (hours after) | Length (cm) | Condition of feces | | | | | | | | |
|---|---|---|---|---|---|---|---|---|---|---|---|---|
| | | | | Hardness | | | | | Space | | | |
| | Agent | | | Hard | Normal | Slightly soft | Soft | Muddy | Regular | Irregular | Extraordinary | Muddy |
| Group 5 | Ery | 6 | 1.3 ± 1.9 | 0 | 0 | 0 | 3 | 7 | 0 | 0 | 0 | 10 |
| Group 6 | Ery | 12 | 66.0 ± 12.1 | 0 | 10 | 0 | 0 | 0 | 0 | 9 | 1 | 0 |

Ery: erythritol 2.8 g/kg

The hardness of feces was determined during perfusion.

a) Hardness of Feces

Normal feces were shown in all animals in control group. In E1H and E2H groups, normal feces were found near the rectum and feces gradually became muddy. In E3H and E6H groups, all feces were muddy. One animal out of 5 in E6H group slightly recovered from muddy feces, though the feces of 4 animals remains muddy. In E12H group, feces of most normal hardness were formed in all animals.

b) Length of Formed Feces, the Space Between Feces, and Alignment Condition

In control group, the length of feces was 55.0±8.8 cm, the size of feces was constant and the space was regular. In E1H group, the feces was partially soft, the size was irregular, the space was also irregular such as extraordinary and the length of formed feces was 22.8±6.9 cm. In E2H to E6H groups, the intestine was filled with muddy feces or nearly soft feces, and the length of formed feces was 0 cm. In E12H group, feces having almost regular shapes were formed and their length was 66.0±12.1 cm. The spaces of feces were about 0.7 to 1 cm in control group; however was 8 to 10 cm in part of E12H group. The generation of gas was observed in the space of feces by paracentesis.

According to the results above, diarrhea caused by the administration of erythritol became severe 2 to 3 hours after and it continued up to 6 hours after, and then the animal almost recovered 12 hours after.

B) Endolymphatic Hydrops Decompression Effect Correlation Between the Extension of Membrane and the Increased Area in Operated Side The average ±standard deviation of IR-L and IR-S in the operated side are shown in Table 15. IR-L and IR-S in right side (control) of the same animals were also determined as controls, i.e. no treating group. The result is also shown in Table 15.

TABLE 15

Time-cource of the endolymphatic hydrops decompression effect after the administration of erythritol
Group 2-1

| | | | Agent | Perfusion (hours after) | IR-L (%) | IR-S (%) |
|---|---|---|---|---|---|---|
| Group 1 | Control | Control side | Distilled water | 3 | 2.4 ± 1.7 | 6.5 ± 3.1 |
| Group 1 | Control | Operated side | Distilled water | 3 | 34.2 ± 33.8 | 45.4 ± 41.3 |
| Group 2 | E1H group | Operated side | Ery | 1 | 24.2 ± 20.2 | 32.1 ± 23.3 |
| Group 3 | E2H group | Operated side | Ery | 2 | 29.4 ± 25.5 | 30.2 ± 26.3 |
| Group 4 | E3H group | Operated side | Ery | 3 | 23.2 ± 16.9 | 32.7 ± 22.4 |
| Group 5 | E6H group | Operated side | Ery | 6 | 37.8 ± 24.8 | 51.4 ± 38.1 |
| Group 6 | E12H group | Operated side | Ery | 12 | 37.5 ± 18.7 | 51.4 ± 22.5 |

No hydrops was formed in the control side of the control group. In the operated side, the degree of experimental hydrops formation by the atresia surgery to more than 100%. Therefore it is difficult to assess the effect of erythritol and its time-course by comparing averages ±standard deviation of IR-L and IR-S.

FIG. 1 shows scattergram and regression lines of the increase ratio of the length of Reissner's membrane (IR-L) and the increase ratio of the cross-sectional area of the scala media (IR-S) of the operated ears of in each animals; the sequential changes of the decompression after the administration of erythritol. ○ (opening circle):IR-S (distilled water) vs IR-L (distilled water), □(opening square): IR-S (1 hour after) vs IR-L (1 hour after), (left side opening and right side filled circle): IR-S (2 hours after) vs IR-L (2 hours after), ● (filled circle): IR-S (3 hours after) vs IR-L (3 hours after), x: IR-S (6 hours after) vs IR-L (6 hours after), ■ (filled square): IR-S (12 hours after) vs IR-L (12 hours after). Since almost no difference is shown in the regression lines of each group, it cannot be understood that there is the decompression effect of erythritol alone. When endolymphatic hydrops is formed, the cross-sectional area of scala media and the length of Reissner's membrane will increase. It can be assumed from FIG. 1 that there is statistically a primary correlation between both of them in the operated side in the control group. The regression lines are; IR-S (distilled water)=4.011+1.212*IR-L (distilled water); R2=0.987, IR-S (1 hour after)=5.409+1.1*IR-L (1 hour after); R2=0.903, IR-S (2 hours after)=1.125+ 0.992*IR-L (2 hours after); R2=0.98, IR-S (3 hours after)= 2.407+1.309*IR-L (3 hours after); R2=0.974, IR-S (6 hours after)=7.36+1.147*IR-L (6 hours after); R2=0.895, IR-S (12 hours after)=8.089+1.152*IR-L (12 hours after); R2=0.918. When hydrops are decompressed by the administration of agents, the regression line shifts downward, because the increase ratio of the cross-sectional area of the scala media reduces while the area of the membrane increases.

There is no significant difference between the regression lines of 5 groups, i.e. control and E1H to E12H groups in FIG. 1 (ANCOVA test). This result suggests that there is no decompression effect by administering saccharides or sugar alcohols alone. This is because the p-AVP (=ADH: antidiuretic hormone in plasma) is elevated by the dehydration caused by the cathartic action (Safwate A et al: Br Vet J 147: 533-7, (1991)).

This suggests that in order to ensure the endolymphatic hydrops decompression effect of saccharides or sugar alcohols, the cathartic effect of saccharides or sugar alcohols have to be inhibited.

(2) Group 2-2: Erythritol Added Pectin

One month after the surgical obliteration of the endolymphatic sac in the left ear, 40 guinea pigs were divided into 4 groups, wherein each group includes 10 animals, and then were administered agents as shown below. Animals were sacrificed 3 hrs or 6 hrs after administration.

TABLE 16

| Groups | Agents | Perfusion(After administration) |
|---|---|---|
| [2-2-a: Dose-depending effect of pectin] | | |
| Group 7: E + P 0.1 g | Ery 2.8 g/kg + P0.1 g/kg | 3 hours after |
| Group 8: E + P3H | Ery2.8 g/kg + P0.5 g/kg | 3 hours after |
| [2-2-b: Time-depending effect of pectin 0.5 g/kg] | | |
| Group 9: E + P6H | Ery2.8 g/kg + P0.5 g/kg | 6 hours after |
| Group 10: E + P12H | Ery2.8 g/kg + P0.5 g/kg | 12 hours after |

The single dose was 8 ml/kg in groups 7 to 10.

The symptoms of large intestine, colon and rectum, in particular the conditions of formed feces were observed. The decalcification, the dehydration, the embedding, the staining, the observation and measurement under light microscope were performed as previously described in Group 2-1.

A) Gastrointestinal Conditions

The hardness and spaces of feces and the length of formed feces in 2 groups divided as above were determined.

[2-2-a: Dose-Depending Effect of Pectin 3 Hours after the Administration]

The result is shown in Table 17.

TABLE 17

Group 2-2: Erythritol added pectin
2-2-a: Dose-depending effect of pectin 3 hours after the administration

| | | | | Condition of feces | | | | | | | |
|---|---|---|---|---|---|---|---|---|---|---|---|
| | | Perfusion | | | Hardness | | | | | Space | |
| | Agent | (hours later) | Length (cm) | Hard | Normal | Slightly soft | Soft | Muddy | Regular | Irregular | Extraordinary | Muddy |
| Group 4 | Ery | 3 | 0 | 0 | 0 | 0 | 0 | 10 | 0 | 0 | 0 | 10 |
| Group 7 | Ery + P: 0.1 g/kg | 3 | 7.3 ± 13.3 | 0 | 0 | 2 | 3 | 5 | 0 | 2 | 3 | 5 |
| Group 8 | Ery + P: 0.5 g/kg | 3 | 19.2 ± 21.7 | 0 | 4 | 1 | 2 | 3 | 0 | 4 | 3 | 3 |

Muddy feces were shown in all 10 animals in Group 4 of Group E3H (Erythritol without pectin). Muddy feces were shown in 5 animals out of 10 in Group 7 (Group E+P0.1 g: erythritol added 0.1 g/kg of pectin) and soft feces in 3 animals, which had feces of 2 to 3 cm from anus. Remaining 2 animals had slightly soft-shaped feces of 23 cm and 42 cm, respectively. The spaces between feces were irregular, for example more than 10 cm. The average length of shaped feces among 10 animals was 7.3±13.3 cm. Muddy feces were found in 3 animals, soft and slightly soft feces were observed in 1 animal, respectively and normal feces in 3 animals in Group 8 (E+P3H group: erythritol added 0.5 g/kg of pectin). The significant anti-diarrhea effect was recognized (p<0.01, Mann-Whitney test). However, the spaces between feces in the animals were not regular. The average length of shaped feces in 10 animals was 19.2±21.7 cm.

Reference) Effect on Systemic Condition Secondary to Diarrhea

Subject and Method)

Twelve guinea pigs (280 to 320 mg of body weight, normal feces) were divided into 3 groups. Only distilled water was administered to the animals in Group 1, erythritol+pectin (0.1 g/kg) to Group 2, and erythritol+pectin (0.5 g/kg) to Groups 3. Three hours after the administration, the animals were sacrificed and bloods were collected. The plasma AVP level were investigated as previously described in Non-patent Reference 8

The agents to be administered and the results are shown in Table 18. 2.8 g/kg of Erythritol is administered. The single dose of the solution was 8 ml/kg.

TABLE 18

Agents and Plasma AVP

| Agents | Plasma AVP | Osmotic pressure of plasma | Condition of feces | Remarks |
|---|---|---|---|---|
| Distilled water | 1.93 ± 0.75 | 307.8 ± 5.3 | Normal: 4 | Corresponding to Group 1 |
| Ery + P0.1 g/kg | 14.78 ± 10.72 | 337.8 ± 27.5 | Soft: 2, Muddy: 2* | Corresponding to Group 7 |
| Ery + P0.5 g/kg | 5.20 ± 3.8 | 323.0 ± 9.8 | Normal 3, Soft: 1** | Corresponding to Group 8 |

Ery: erythritol (2.8 g/kg)

*The p-AVP of animals excreting soft feces were 3.2 and 8.3, and those of muddy feces were 25.5 and 22.1.
Unit: pg/ml

**The p-AVP of animals excreting soft feces were 10.9 and those of normal feces were 3.1, 2.8 and 4.0.

The severity of diarrhea is proportional to the level of p-AVP.

When saccharides or sugar alcohols added about 3.6% by weight of polysaccharides (pectin 0.1 g/kg) were administered, severe diarrhea and high p-AVP level was ascertained (cf. Table 17). On the other hand, when the formulation of the present invention was administered, normal feces were shown in 3 animals out of 4 and the p-AVP level was decreased (cf. Table 18).

As shown in Table 1, IR-S is proportional to the p-AVP.

When erythritol added 0.1 g/kg of pectin (about 3.6% by weight) was administered, the p-AVP was high and the decompression effect of endolymphatic hydrops was not shown. When erythritol added 0.5 g/kg of pectin was administered, the p-AVP was low and the remarkable decompression effect was shown. This result is consistent with Non-patent Reference 10.

When small amount of polysaccharides are added to erythritol and administered, diarrhea followed by dehydration is developed. Polysaccharides at as low concentration as those used as suspending agents or thickners induce increased p-AVP and result in the formation of endolymphatic hydrops, which is the pathology of Meniere's disease (a severe state that has p-AVP level as high as that during a paroxysmal phase).

[2-2-b: Erythritol added 0.5 g/kg of Pectin is Administered and Time-Course Thereafter]

The result is shown in Table 19.

TABLE 19

2-2-b: Difference in feces after the administration of 0.5 g/kg of pectin

| | | | | Condition of feces | | | | | | | | |
|---|---|---|---|---|---|---|---|---|---|---|---|---|
| | | | | | Hardness | | | | | Space | | |
| | | Perfusion | | | | Slightly | | | | | | |
| | Agent | (hours after) | Length (cm) | Hard | Normal | soft | Soft | Muddy | Regular | Irregular | Extraordinary | Muddy |
| Group 8 | Ery + P: 0.5 g/kg | 3 | 19.2 ± 21.7 | 0 | 4 | 1 | 2 | 3 | 0 | 4 | 3 | 3 |
| Group 9 | Ery + P: 0.5 g/kg | 6 | 30.8 ± 23.5 | 0 | 6 | 1 | 2 | 1 | 0 | 7 | 2 | 1 |
| Group 10 | Ery + P: 0.5 g/kg | 12 | 45.4 ± 11.5 | 0 | 10 | 0 | 0 | 0 | 10 | 0 | 0 | 0 |

The hardness of feces was determined during perfusion. Muddy feces were shown in 3 animals and normal feces in 4 animals in Group 8 in 2-2-a (E+P3H group: sacrificed 3 hours after). Muddy feces were shown in one, soft feces in 2, slightly soft feces in one and normal feces were shown in other 6 animals in Group 9 (E+P6H group; sacrificed 6 hours after the administration). Muddy feces were shown in 7 animals in Group 5 which erythritol (E6H group) alone were administered. The antidiarrheal effect of pectin was shown ($p<0.01$, Mann-Whitney test). The spaces were still irregular and the length of shaped feces was 30.8±23.6 cm (average of 10 animals). It appears that the diarrhea is transient, because an animal excreting muddy or soft feces near rectum has almost normal feces near colon.

Normal feces and regular spaces of feces were shown in all animals in Group 10 (E+P12H group: perfusion 12 hours after). The alignment of feces was regular, suggesting significant improvement in comparison with Group 6 (E12H group) where 9 animals out of 10 showed irregular ($p<0.001$, Mann-Whitney test). This result suggests improvement of the unpleasant gastrointestinal symptoms such as intestinal abnormal fermentation. The average length of shaped feces was 45.4±11.5 cm.

B) Endolymphatic Hydrops Decompression Effect

The difference of decompression effect on endolymphatic hydrops depending on dose of pectin added and time-course of the decompression effect can hardly determined by comparing and analyzing the average and standard deviation of IR-L and IR-S in the operated side in each groups. Therefore as determined in Group 1, those were determined by comparing the slopes of lines and Y-intercepts in FIGS. 2 and 3.

[2-2-a: Difference of Effect Depending on the Dose of Pectin 3 Hours after the Administration is Determined]

Figure 2:
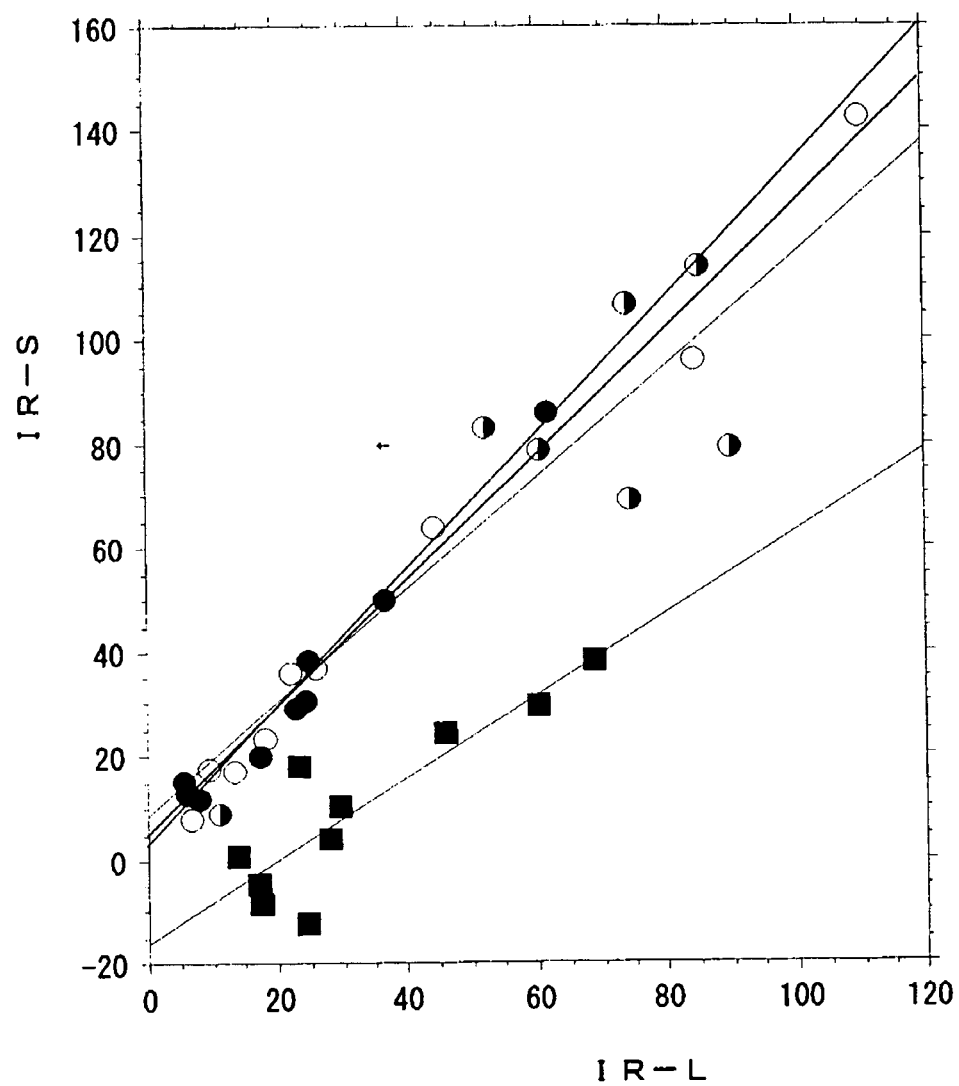
FIG. 2 shows scattergram and regression lines of the IR-L and IR-S of the operated ears of Group 1, 2-1 in Example 2 for the difference of the amount of polysaccharides (pectin) as the additives to show the difference of the decompression effects in the operated side based on the difference of the amount of pectin.

The average and standard deviation of IR-L and IR-S in each group are shown in Table 20. FIG. 2 shows a scattergram and regression lines thereof.

TABLE 20

2-2-a: Difference of endolymphatic hydrops decompression effect
depending on the dose of pectin 3 hours after the administration

|  |  | Agent | Perfusion (After administration) | Operated side IR-L (%) | IR-S (%) |
|---|---|---|---|---|---|
| Group 1 | Control | distilled water | 3 hours after | 34.2 ± 33.8 | 45.4 ± 41.3 |
| Group 4 | E3H group | Ery | 3 hours after | 23.2 ± 16.9 | 32.7 ± 22.4 |
| Group 7 | E + P0.1 group | Ery: +P: 0.1 g/kg | 3 hours after | 63.8 ± 24.7 | 77.3 ± 31.6 |
| Group 8 | E + P3H group | Ery: +P: 0.5 g/kg | 3 hours after | 32.9 ± 18.0 | 10.1 ± 16.2 |

No significant difference is shown between E3H group (erythritol alone) and control group (distilled water) in FIG. 2, as shown in Group 1. Also no significant difference is shown between Group 7 (erytiritol added 0.1 g/kg of pectin), E3H group and control group. However since significant difference is shown in Group 8 (erythritol added 0.5 g/kg of pectin) (p<0.001), significant decompression effect is shown in Group 8. ○ (opening circle): IR-S (distilled water) vs IR-L (distilled water), ● (filled circle): IR-S (E3H) vs IR-L (E3H), (left side opening and right side filled circle): IR-S (E+P0.1 g) vs IR-S (E+P0.1 g), ■ (filled square): IR-S (E+P0.5 g) vs IR-L (E+P0.5 g). IR-S (distilled water)=4.011+1.212*IR-L (distilled water); R2=0.987, IR-S (erythritol, 3 hours after)= 2.407+1.309*IR-L (erythritol, 3 hours after); R2=0.974, IR-S (erythritol+pectin 0.1 g)=8.683+1.074*IR-L (erythritol+pectin 0.1 g); R2=0.704, IR-S (erythritol+pectin 0.5 g)=−15.925 +0.79*IR-L (erythritol+pectin 0.5 g); R2=0.771.

No significant difference is shown between Group 7 (erythritol added 0.1 g/kg of pectin about 3.6% by weight), control group (distilled water) and E3H group (administered with erythritol alone) (ANCOVA test). On the other hand, Group 8 (administered with erythritol added 0.5 g/kg of pectin) shifts downward compared with control group and E3H group (p<0.01 and p<0.05, respectively, ANCOVA test). This result suggests that no decompression effect is shown at the concentration as high as those conventionally used as suspending agents, emulsifiers or stabilizing agents, such as less than 1% and that only when pectin is added at or more than 0.5 g (17.9% by weight) significant decompression effect can be achieved In table 20, IR-L and IR-S in Group 7 are greater than other groups. This is because higher hydrops formation by the atresia surgery is caused by individual differences. Since no significant difference is shown according to FIG. 2, this is not exacerbation of hydrops due to the administration of agents.

[2-2-b: Time-Course after the Administration of Erythritol Added 0.5 g/Kg of Pectin is Determined]

Figure 3:
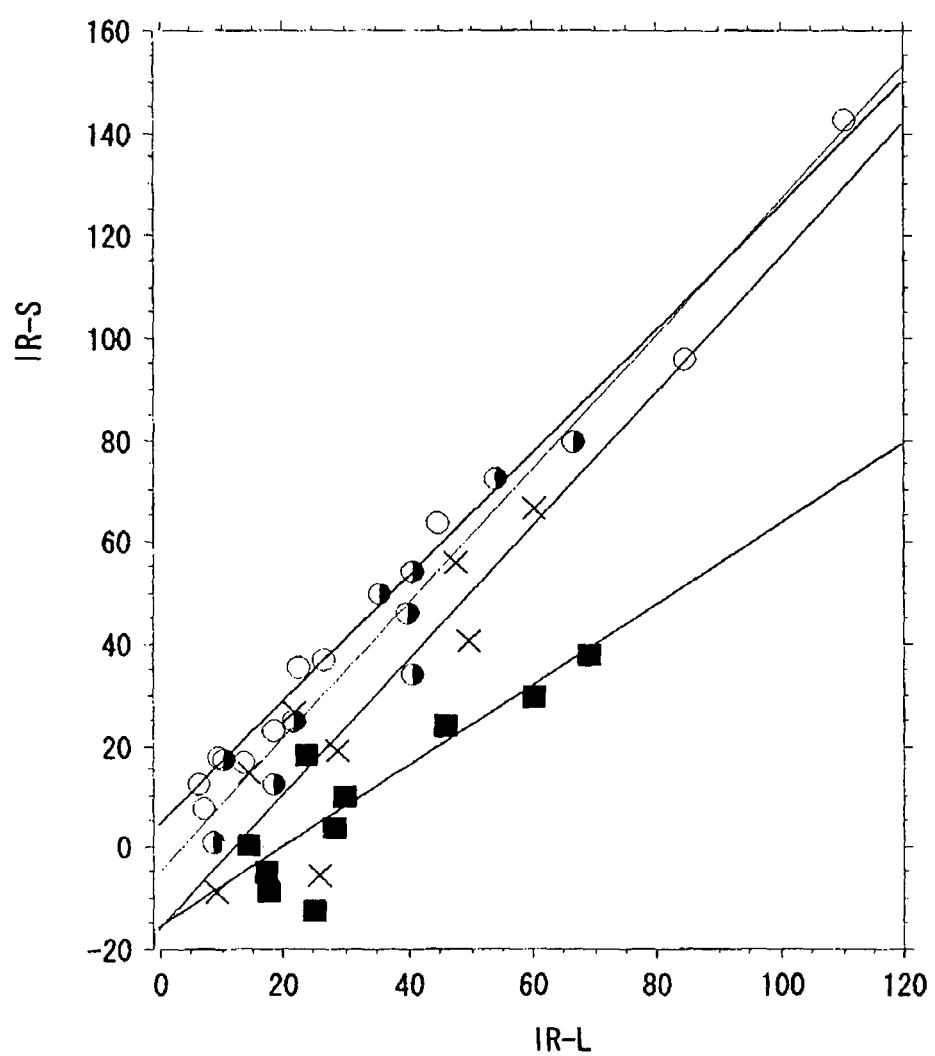
FIG. 3 shows scattergram and regression lines of the sequential changes of IR-L and IR-S of the operated ear of Example 2: Group 2, 2-2: Group 8 (pectin 0.5 g/kg, after 3 hours) for the sequential change after the administration of erythritol and polysaccharides (pectin 0.5 g/kg).

The average and standard deviation of IR-L and IR-S in each group are shown in Table 21. FIG. 3 shows a scattergram and regression lines thereof.

TABLE 21

2-2-b: Time-cource or decompression effect after the
administration of erythritol added pectin (0.5 g/kg)

|  | Agent |  | Perfusion (after the administration) | Operated side IR-L (%) | IR-S (%) |
|---|---|---|---|---|---|
| Group 8 | E + P3H group | Ery: +P: 0.5 g/kg | 3 hours after | 32.9 ± 18.0 | 10.1 ± 16.2 |
| Group 9 | E + P6H group | Ery: +P: 0.5 g/kg | 6 hours after | 32.3 ± 17.1 | 26.0 ± 25.4 |
| Group 10 | E + P12H group | Ery: +P: 0.5 g/kg | 12 hours after | 32.5 ± 17.8 | 42.7 ± 26.5 |

Since significant difference is shown between Group 9 (6 hours after) and control group (p<0.001), the decompression effect is present, however such decompression effect is significantly lower than that of Group 8 (3 hours after) (p<0.05). In Group 10 (10 hours after) the decompression effect furthermore decreases significantly and thus no significant difference is shown in comparison to control group (distilled water). This result suggests that the decompression effect decreases over time and the effect disappears 12 hours after. ○ (opening circle): IR-S (distilled water) vs IR-L (distilled water), ■ (filled square): IR-S (E+P3H) vs IR-L (E+P3H), x: IR-S (E+P6H) vs IR-L (E+P6H), (left side opening and right side filled circle): IR-S (E+P12H) vs IR-L (E+P12H). IR-S (distilled water)=4.011+1.212*IR-L (distilled water); R2=0.987, IR-S (erythritol+pectin, 3 hours after)=−15.925 + 0.79*IR-L (erythritol+pectin, 3 hours after); R2=0.771, IR-S (erythritol+pectin, 6 hours after)=−16.508 +1.314*IR-L (erythritol+pectin, 6 hours after); R2=0.784, IR-S (erythritol+pectin, 12 hours after)=−4.58+1.314*IR-L (erythritol+pectin, 12 hours after); R2=0.913.

In Group 8 (3 hours after), significant decompression is shown in comparison with control group (distilled water) and E3H group (erythritol alone) in FIG. 3 as described in 2-2-a. Also, in Group 9 (6 hours after), significant decompression is shown in comparison with control group and E3H group ($p<0.001$). The line of Group 9 shifts upward significantly compared with that of Group 8 ($p<0.05$). In group 10 (12 hours after), significant difference is shown in comparison with E3H group and E6H group ($p<0.001$ and $p<0.01$, respectively), though no significant difference with control group and E3H group. As the result, 3 hours after the administration the decompression effect becomes maximum, the decompression effect is still present 6 hours after, however the effect is lower than that 3 hours after, and 12 hours after the property disappears.

(3) Group 2-3

Another combination of saccharides or sugar alcohols and polysaccharides was prepared to determine the anti-diarrhea effect thereof according to the criteria of Table 2. After 1 month of the left side endolymphatic sac atresia surgery, animals were received saccharides or sugar alcohols and polysaccharides. Three hours after the administration (when the cathartic effect of saccharides or sugar alcohols and polysaccharides becomes maximum), the animals were sacrificed. A temporal bone was removed from the animals. The preparation was performed as previously described in Non-patent Reference 8 to observe the inner ears and to determine and evaluate the endolymphatic hydrops decompression effect.

2-3-a) Xylitol Added Xanthan Gum

Twelve guinea pigs were divided into 2 groups (6 in each), and then were administered agents as described below. Three hours after the administration, animals were sacrificed.

TABLE 22

| Group | Agents | Perfusion (after the administration) |
|---|---|---|
| Group 11 | xylitol (2.8 g/kg) alone | 3 hours after |
| Group 12 | xylitol (2.8 g/kg) + xanthan gum (0.2 g/kg) | 3 hours after |

Among these results, the assessment of the antidiarrheal effect is shown in Table 23.

TABLE 23

| | Saccharide or sugar alcohol | Dosage | Additives | | Number of animals | Hardness of feces | | | |
|---|---|---|---|---|---|---|---|---|---|
| | | | | | | 3 | 2 | 1 | 0 |
| Group 11 | xylitol alone | 2.8 g/kg | — | — | 6 | 0 | 2 | 3 | 2 |
| Group 12 | xylitol + XG | 2.8 g/kg | XG | 0.2 g/kg | 6 | 4 | 1 | 1 | 0 |

The antidiarrheal effect is produced by adding xanthan gum (7.1% by weight) to xylitol (p<0.05, Mann-Whitney test).

Figure 4:
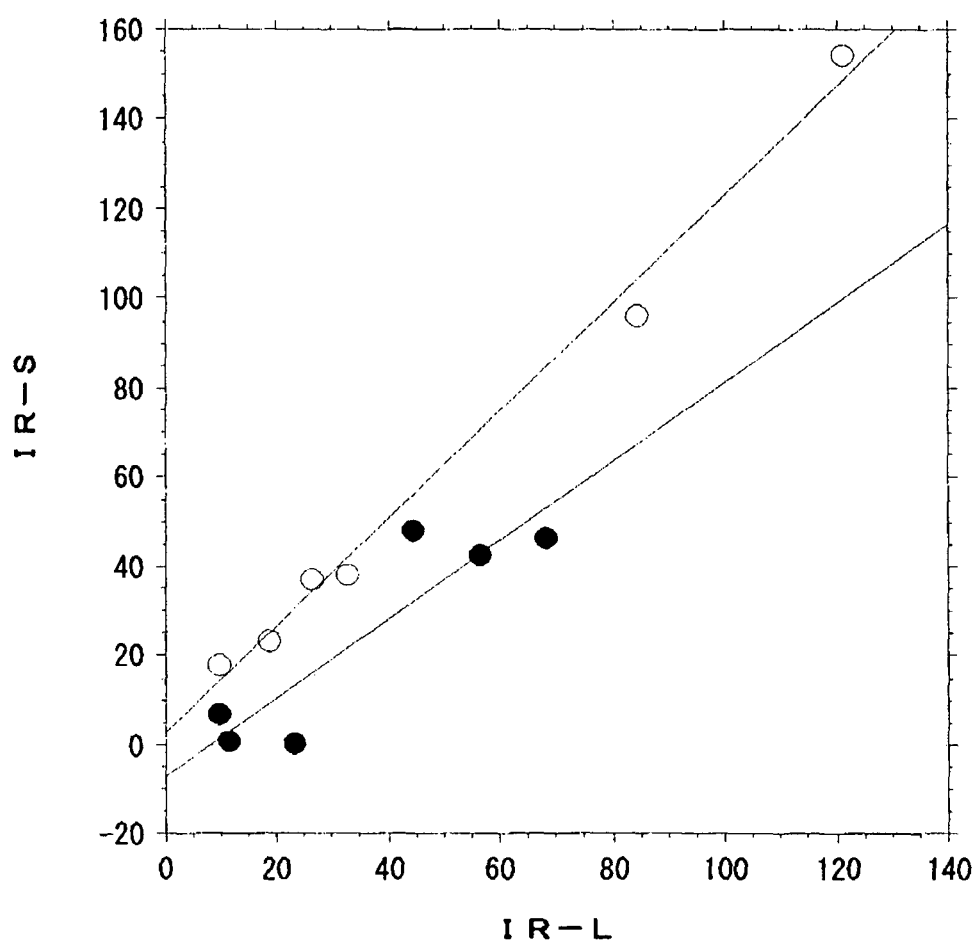
FIG. 4 indicates the IR-L and IR-S of the group administering xylitol alone and the group administering added xanthan gum as a polysaccharide.

The results of morphological observation is shown in Table 24 and FIG. 4.

TABLE 24

|  | Agent | Perfusion (after the administration) | Operated side IR-L (%) | IR-S (%) |
|---|---|---|---|---|
| Group 11 | XL alone | 3 hours after | 48.6 ± 40.3 | 60.1 ± 48.9 |
| Group 12 | XL + XG | 3 hours after | 35.3 ± 22.2 | 24.0 ± 21.7 |

FIG. 4 suggests that when xanthan gum is added as polysaccharides, significant decompression effect on endolymphatic hydrops is shown in comparison with the group administered with xylitol alone (p<0.01, ANCOVA test).

In FIG. 4, ○ (opening circle): IR-S (xylitol alone) vs IR-L (xylitol alone), ●: IR-S (xylitol+xanthan gum) vs IR-L (xylitol+xanthan gum). The regression lines are IR-S (xylitol alone)=2.371+1.208* IR-L(xylitol alone); R2=0.991, IR-S (xylitol+xanthan gum)=−7.154 +0.882* IR-L (xylitol+xanthan gum); R2=0.82.

2-3-b) Isosorbitol Added Sodium Alginate

Fifteen guinea pigs were divided into 2 groups, and then were administered agents as described below. Three hours after the administration, the animals were sacrificed.

TABLE 25

| Group | Agent | Perfusion (after the administration) |
|---|---|---|
| Group 13 (8 animals) | IB (2.8 g/kg) alone | 3 hours after |
| Group 14 (7 animals) | IB (2.8 g/kg) + sodium alginate (0.3 g/kg) | 3 hours after |

Among these results, the assessment of the antidiarrheal effect is shown in Table 26.

TABLE 26

|  | Saccharide or sugar alcohol | Dosage | Additives | | Number of animals | Hardness of feces | | | |
|---|---|---|---|---|---|---|---|---|---|
|  |  |  |  |  |  | 3 | 2 | 1 | 0 |
| Group 13 | IB alone | 2.8 g/kg | — |  | 8 | 2 | 2 | 3 | 1 |
| Group 14 | IB + Al | 2.8 g/kg | Al | 0.3 g/kg | 7 | 6 | 1 | 0 | 0 |

The antidiarrheal effect is shown by adding sodium alginate (10.7% by weight) (p<0.05, Mann-Whitney test).

Figure 5:
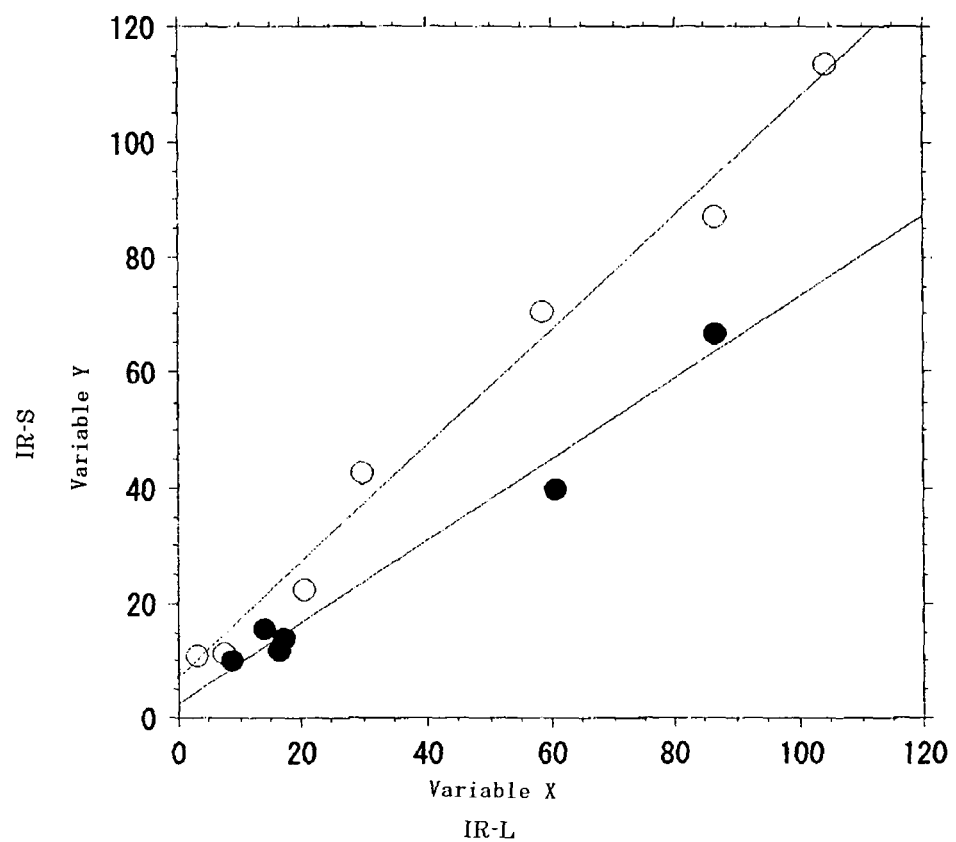
FIG. 5 indicates the IR-L and IR-S of the group administering isosorbitol alone and the group administering added sodium alginate as a polysaccharide.

The results of morphological observation is shown in Table 27 and FIG. 5.

TABLE 27

|  | Agent | Perfusion (after the administration) | Operated side IR-L (%) | IR-S (%) |
|---|---|---|---|---|
| Group 13 | IB alone | 3 hours after | 31.3 ± 36.5 | 40.9 ± 38.2 |
| Group 14 | IB + Al | 3 hours after | 34.4 ± 27.1 | 27.5 ± 19.5 |

In group 2 where sodium alginate is added as polysaccharides, decompression effect on endolymphatic hydrops is shown (p<0.01).

In FIG. 5, ○ (opening circle): IR-S (isosorbitol alone) vs IR-L (isosorbitol alone), ●: IR-S (isosorbitol+sodium alginate) vs IR-L (isosorbitol+sodium alginate). The regression lines are IR-S (isosorbitol alone)=7.143+1.003* IR-L (isosorbitol alone); R2=0.985, IR-S (isosorbitol+sodium alginate)= 2.691 +0.704* IR-L (isosorbitol+sodium alginate); R2=0.977, respectively.

2-3-c) Isosorbitol Added Agar

Fifteen guinea pigs were divided into 2 groups, and then were administered agents as described below. Three hours after the administration, animals were sacrificed.

TABLE 28

| Group | Agent | Perfusion (after the administration) |
|---|---|---|
| Group 13 (8 animals) | IB alone (2.8 g/kg) | 3 hours after |
| Group 15 (7 animals) | IB (2.8 g/kg) + agar (0.3 g/kg) | 3 hours after |

Among these results, the assessment of the anti-diarrhea effect is shown in Table 29.

TABLE 29

| | Saccharide or sugar alcohol | Dosage | Additives | | Number of animals | Hardness of feces | | | |
|---|---|---|---|---|---|---|---|---|---|
| | | | | | | 3 | 2 | 1 | 0 |
| Group 13 | IB alone | 2.8 g/kg | — | — | 8 | 2 | 2 | 3 | 1 |
| Group 15 | IB + agar | 2.8 g/kg | agar | 0.3 g/kg | 7 | 5 | 2 | 0 | 0 |

The antidiarrheal effect is shown by adding agar (10.7% by weight) to IB ($p<0.05$, Mann-Whitney test).

Figure 6:
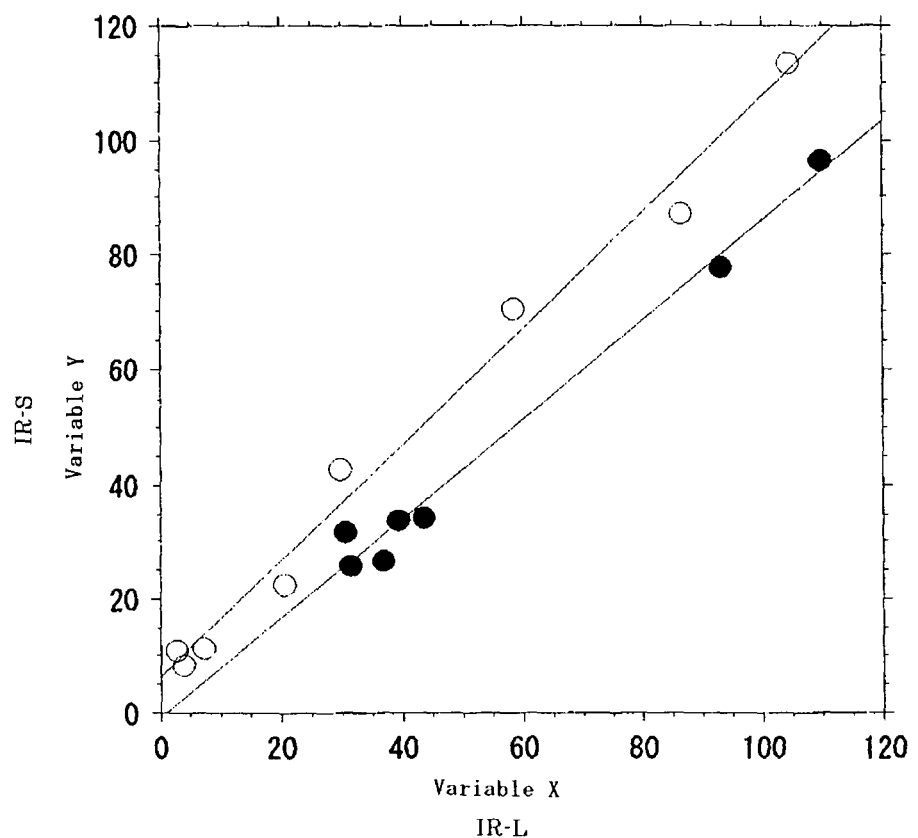
FIG. 6 indicates the membrane and the area changes in the group administering isosorbitol alone and the group administering added agar as a polysaccharide.

The results of morphological observation is shown in Table 30 and FIG. 6.

TABLE 30

| | Agent | Perfusion (after the administration) | Operated side IR-L (%) | IR-S (%) |
|---|---|---|---|---|
| Group 13 | IB alone | 3 hours after | 31.3 ± 36.5 | 40.9 ± 38.2 |
| Group 15 | IB + agar | 3 hours after | 47.9 ± 33.5 | 41.0 ± 29.0 |

In group 2 where agar is added as polysaccharides to IB, significant decompression effect on endolymphatic hydrops is shown ($p<0.01$).

In FIG. 6, ○ (opening circle): IR-S (isosorbitol alone) vs IR-L (isosorbitol alone), ●: IR-S (isosorbitol+agar) vs IR-L (isosorbitol+agar). The regression lines are IR-S (isosorbitol alone)=6.542+1.011* IR-L (isosorbitol alone); $R2=0.987$, IR-S (isosorbitol+agar)=−0.574 +0.865* IR-L (isosorbitol+agar); $R2=0.984$, respectively.

2-3-d) Glycerol Added Sodium Carboxymethyl Cellulose

Twelve guinea pigs were divided into 2 groups, and then were administered agents as described below. Three hours after the administration, animals were sacrificed.

TABLE 31

| Group | Agent | Perfusion (after the administration) |
|---|---|---|
| Group 16 (6 animals) | glycerol (2.8 g/kg) alone | 3 hours after |
| Group 17 (6 animals) | glycerol (2.8 g/kg) + CMC (0.28 g/kg) | 3 hours after |

Among these results, the assessment of the antidiarrheal effect is shown in Table 32.

TABLE 32

| | Agent | Dosage | Additives | | Number of animals | Hardness of feces | | | |
|---|---|---|---|---|---|---|---|---|---|
| | | | | | | 3 | 2 | 1 | 0 |
| Group 16 | Gly alone | 2.8 g/kg | — | | 6 | 0 | 2 | 3 | 1 |
| Group 17 | Gly + CMC | 2.8 g/kg | CMC | 0.28 g/kg | 6 | 5 | 1 | 0 | 0 |

The antidiarrheal effect is shown by adding sodium carboxymethyl cellulose (10% by weight) to glycerol ($p<0.01$, Mann-Whitney test).

Figure 7:
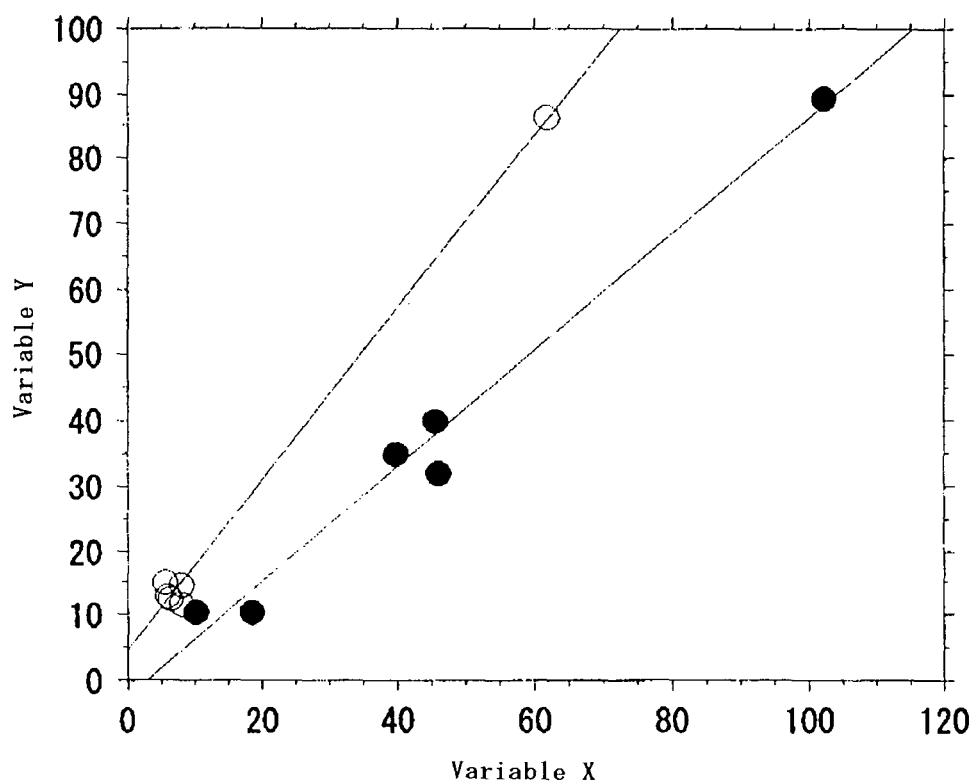
FIG. 7 indicates the IR-L and IR-S of the group administering sole glycerol and the group administering added sodium carboxymethyl cellulose as a polysaccharide.

The results of morphological observation is shown in Table 33 and FIG. 7.

TABLE 33

| | Agent | Perfusion (after the administration) | Operated side IR-L (%) | IR-S (%) |
|---|---|---|---|---|
| Group 16 | Gly alone | 3 hours after | 37.4 ± 31.2 | 31.0 ± 27.5 |
| Group 17 | Gly + CMC | 3 hours after | 13.5 ± 19.9 | 22.0 ± 26.7 |

In the group where sodium carboxymethyl cellulose is added as polysaccharides to glycerol, significant decompression effect on endolymphatic hydrops is shown in comparison with the group administered with glycerol alone ($p<0.01$).

In FIG. 7, ○ (opening circle): IR-S (glycerol alone) vs IR-L (glycerol alone), ●: IR-S (glycerol+sodium carboxymethyl cellulose) vs IR-L (glycerol+sodium carboxymethyl cellulose). The regression lines are area of glycerol alone =−2.455 +0.887*glycerol alone membrane; $R2=0.982$, (glycerol+sodium carboxymethyl cellulose) area=4.806+

1.316* (glycerol+sodium carboxymethyl cellulose) membrane; R2=0.995, respectively.

2-3-e) Xylose Added Xanthan Gum

Twelve guinea pigs were divided into 2 groups, and then were administered agents as described below. Three hours after the administration, animals were sacrificed.

TABLE 34

| Group | Agent | Perfusion (after the administration) |
|---|---|---|
| Group 18 (6 animals) | xylose (2.8 g/kg) alone | 3 hours after |
| Group 19 (6 animals) | xylose (2.8 g/kg) + xanthan gum (0.2 g/kg) | 3 hours after |

Among these results, the assessment of the antidiarrheal effect is shown in Table 35.

TABLE 35

| | Saccharide or sugar alcohol | Dosage | Additives | | Number of animals | Hardness of feces | | | |
|---|---|---|---|---|---|---|---|---|---|
| | | | | | | 3 | 2 | 1 | 0 |
| Group 18 | xylose alone | 2.8 g/kg | — | — | 6 | 0 | 1 | 3 | 1 |
| Group 19 | xylose + XG | 2.8 g/kg | XG | 0.2 g/kg | 6 | 5 | 1 | 0 | 0 |

The antidiarrheal effect is shown by adding xanthan gum (7.1% by weight) to xylose ($p<0.01$, Mann-Whitney test).

Figure 8:
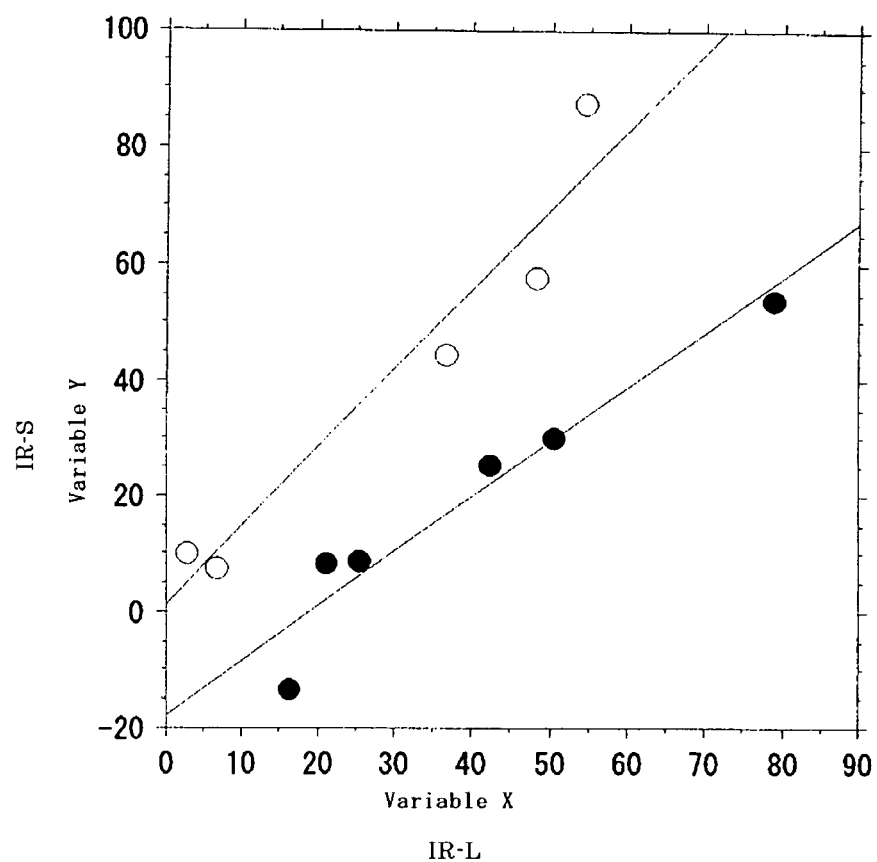
FIG. 8 indicates the membrane and the area changes in the groups administering xylose alone and the group administering added xanthan gum as a polysaccharide.

The results of morphological observation is shown in Table 36 and FIG. 8.

TABLE 36

| | Agent | Perfusion (after the administration) | Operated side IR-L (%) | IR-S (%) |
|---|---|---|---|---|
| Group 18 | xylose alone | 3 hours after | 29.7 ± 21.3 | 41.7 ± 30.1 |
| Group 19 | xylose + XG | 3 hours after | 39.1 ± 21.5 | 19.0 ± 21.0 |

In the group where xanthan gum is added as polysaccharides to xylose, significant decompression effect on endolymphatic hydrops is shown in comparison with the group administered with xylose alone ($p<0.001$).

In FIG. 8, ○ (opening circle): IR-S (xylose alone) vs IR-L (xylose alone), ●: IR-S (xylose+xanthan gum) vs IR-L (xylose+xanthan gum). The regression lines are IR-S (xylose alone)=1.197+1.364* IR-L (xylose alone); R2=0.933, IR-S (xylose+xanthan gum)=17.886 +0.945* IR-L (xylose+xanthan gum); R2=0.93, respectively.

In all groups of Group 2-3, endolymphatic hydrops was decompressed by adding polysaccharides to saccharides or sugar alcohols i.e. the purpose of the present invention was achieved.

EXAMPLE 3

Comparative analysis to currently available Isosorbitol (Kowa Pharmaceutical Co. Ltd., generic name: isosorbide, isosorbitol content: 70%) solution One month after the surgical obliteration of the endolymphatic sac in the left ear, 40 guinea pigs were divided into 4 groups, wherein each group includes 10 animals as shown in Table 36. Groups 20 and 21 received isosorbide formulation (hereinafter, referred to as conventional isosorbitol) and Groups 22 and 23 received the gel formulation comprising isosorbitol (2.8 g/kg), sodium alginate (0.11 g/kg) and inorganic salt (0.09 g/kg). The gastrointestinal symptoms and the decompression effect on endolymphatic hydrops were continued to be observed until the decompression effect of conventional isosorbitol become peak, i.e. for 6 hours (cf. Non-patent Reference 6). Three and six hours after the administration, animals were sacrificed and temporal bones were removed, and then observed, respectively.

In all groups, single dose was 4 ml/kg. The surgical obliteration of the endolymphatic sac, the process for sample preparation and the measurements were performed as previously described in Takeda T: Hear Res. 183: 9-18, (2003).

TABLE 37

| Group | Agent | Perfusion (after the administration) |
|---|---|---|
| Group 13: IB alone | isosorbitol 2.8 g/kg | 3 hours after |
| Group 20: conventional IB | isosorbitol 2.8 g/kg | 3 hours after |
| Group 21: conventional IB | isosorbitol 2.8 g/kg | 6 hours after |
| Group 22: gel formulation | IB 2.8 g/kg + Al + inorganic salt | 3 hours after |
| Group 23: gel formulation | IB 2.8 g/kg + Al + inorganic salt | 6 hours after |

A) Gastrointestinal Condition
Hardness and shapes of feces are shown in Table 38.

and space of feces, p<0.01 and p<0.01 respectively, Mann-Whitney test).

TABLE 38

Difference of conventional IB to <IB + Al> group in the effect on d gastrointestinal system

| | | | | Condition of feces | | | | | | | | |
|---|---|---|---|---|---|---|---|---|---|---|---|---|
| | | | | | Hardness | | | | | Space | | |
| | | | Length | | | Slightly | | | | | | |
| | Agent | Perfusion | (cm) | Hard | Normal | soft | Soft | Muddy | Regular | Irregular | Extraordinary | Muddy |
| Control | Distilled water | 3 hr | 55.0 ± 8.8 | 0 | 10 | 0 | 0 | 0 | 10 | 0 | 0 | 0 |
| Group 13 | IB alone | 3 hr | 24.0 ± 26.6 | 0 | 2 | 2 | 3 | 1 | 0 | 2 | 5 | 1 |
| Group 20 | conventional IB | 3 hr | 38.8 ± 27.3 | 0 | 2 | 3 | 3 | 2 | 0 | 3 | 6 | 1 |
| Group 21 | conventional IB | 6 hr | 60.2 ± 15.8 | 0 | 4 | 3 | 2 | 1 | 1 | 0 | 8 | 1 |
| Group 22 | IB + Al | 3 hr | 32.8 ± 18.9 | 0 | 8 | 2 | 0 | 0 | 3 | 4 | 3 | 0 |
| Group 23 | IB + Al | 6 hr | 61.1 ± 11.4 | 0 | 10 | 0 | 0 | 0 | 6 | 2 | 2 | 0 |

Control: Group 2-1, group 1 in Example 2
IB: isosorbitol 2.8 g/kg
Al: sodium alginate 0.11 g/kg In the groups administered with conventional isosorbitol, feces started to soften 2 hours after or later and the most serious diarrhea condition was developed 3 hours after (Group 20). Normal feces were shown in 2 animals out of 10, slightly soft feces in 3, soft feces in 3 and muddy feces in 2. Six hours after (Group 21) normal feces were shown in 4 animals, slightly soft feces in 3, soft feces in 2 and muddy feces in 1. Compared with the condition 3 hours after the administration, the symptom of diarrhea was improved to some extent; however no significant difference were shown in Groups 20 and 21. Six hours after, the length of formed feces was 60.2±15.8. The space between feces was extraordinary irregular in 8 animals out of 10 and some animals had the space of about 20 to 40 cm. Gas was generated in the intestine. These results suggest severe gastrointestinal symptom. Comparing the hardness and spaces of feces 6 hours after and those in control group, significant difference was shown in both hardness and spaces of feces (p<0.01 and p<0.05, Mann-Whitney test, respectively) suggesting the onset of mild cathartic effect. This result is consistent with the gastrointestinal symptoms such as diarrhea, flatulence, distension and borborygmus, which are sometimes caused by conventional isosorbitol.

On the other hand, in the groups administered with isosorbitol+sodium alginate, slightly soft feces were shown in only 2 animals and normal feces were shown in all the others. Irregular or extraordinary spaces of feces were shown in fewer animals than those administered with conventional isosorbitol. These results suggest that comparing to conventional isosorbitol (Group 20), the antidiarrheal effect is significantly distinct (p<0.05) and the gastrointestinal symptoms are mild (p<0.01, Mann-Whitney test). Six hours after (Group 23), normal hardness of feces was shown in all animals and the spaces were regular in 6 animals. These results suggest that compared with conventional isosorbitol (Group 21), the gastrointestinal symptoms are significantly mild (Hardness B) The Decompression Effect on Endolymphatic Hydrops Decompression Effect
Correlation between IR-L and IR-S in operated side
The result of IR-L and IR-S is shown in Table 39 and FIG. 9.

TABLE 39

Time-cource of the endolymphatic hydrops decompression effect of conventional IB and <IB + Al>

| | Agent | Perfusion | IR-L (%) | IR-S (%) |
|---|---|---|---|---|
| Control | Distilled water | 3 hours after | 30.0 ± 32.3 | 39.4 ± 40.0 |
| Group 13 | IB alone | 3 hours after | 31.3 ± 36.5 | 40.9 ± 38.2 |
| Group 20 | conventional IB | 3 hours after | 48.7 ± 34.1 | 53.5 ± 33.9 |
| Group 21 | conventional IB | 6 hours after | 47.0 ± 32.2 | 39.4 ± 28.6 |
| Group 22 | <IB + Al> | 3 hours after | 33.2 ± 27.1 | 23.4 ± 20.5 |
| Group 23 | <IB + Al> | 6 hours after | 31.2 ± 23.0 | 24.2 ± 17.3 |

IB: isosorbitol 2.8 g/kg [Unit: cm]

Figure 9:
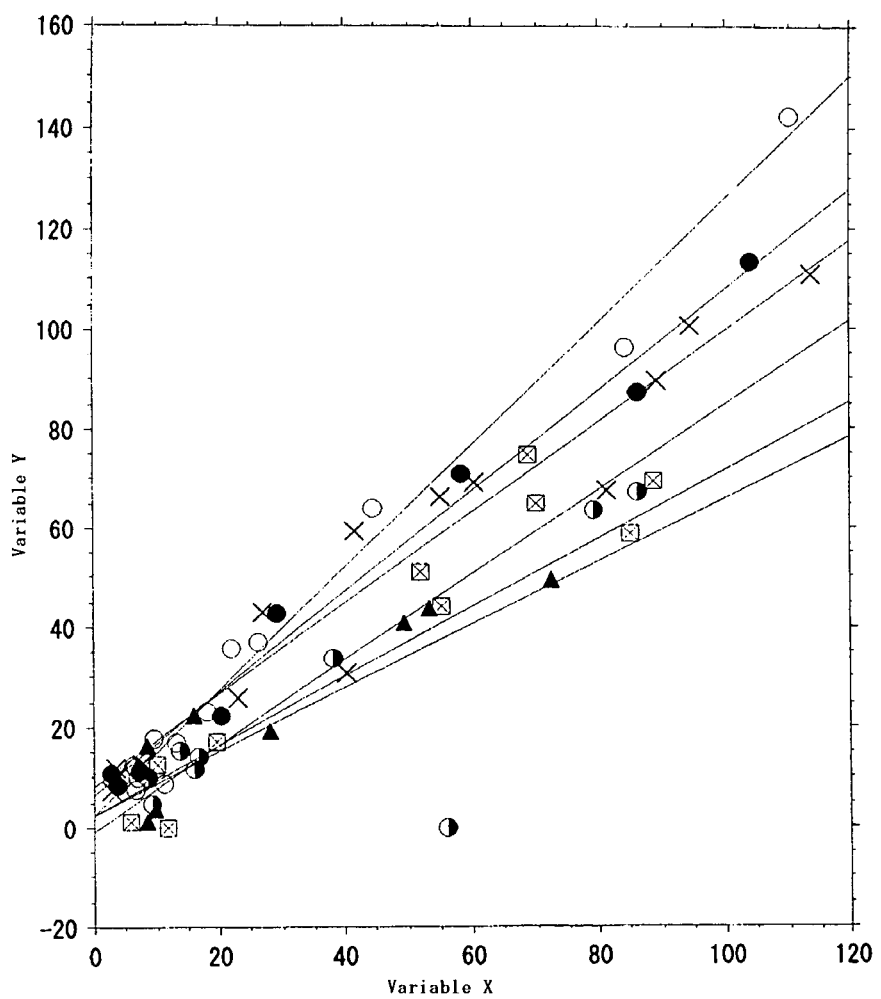
FIG. 9 indicates IR-L and IR-S to show the differences in the decompression effects on the operated side between the product of the present invention and the conventional product in Example 2.

In FIG. 9, ○ (opening circle): IR-S vs IR-L in Group 1 (distilled water), x: IR-S vs IR-L of Group 2 (3 hours after the administration of conventional isosorbitol), (square filled with x): Group 3 IR-S vs IR-L of (6 hours after the administration of conventional isosorbitol), (left side opening and right side filled circle): IR-S vs IR-L of Group 4 (3 hours after the administration of isosorbitol+sodium alginate), ▲ (filled triangle): IR-S vs IR-L of Group 3 (6 hours after the administration of isosorbitol+sodium alginate), ●(filled circle) IR-S vs IR-L of isosorbitol alone. The regression lines are IR-S (distilled water)=2.537+1.23*IR-L(distilled water); $R^2$=0.984, IR-S (3 hours after the administration of isosorbitol+sodium alginate)=2.387 +0.633* IR-L (3 hours the administration of isosorbitol+sodium alginate); $R^2$=0.651, IR-S (6 hours after the administration of isosorbitol+sodium alginate)=2.62 +0.69* IR-L (6 hours after the administration of isosorbitol+sodium alginate); $R^2$=0.881, IR-S (3 hours after the administration of conventional isosorbitol)=8.033 +0.911* IR-L (3 hours after the administration of conventional isosorbitol); $R^2$=0.947, IR-S (6 hours after the administration of conventional isosorbitol)=−0.797 +0.855* IR-L (6 hours after the administration of conventional isosorbitol);

R2=0.907, area of isosorbitol alone=6.542+1.011*IR-L(isosorbitol alone); R2=0.987, respectively.

In FIG. 9, the regression lines of Group 20 (3 hours after the administration of conventional isosorbitol) and 21 (6 hours after the administration of conventional isosorbitol) shift downward compared with the regression line of control group administered with distilled water (Group 1). The differences were significant (p<0.01 and p<0.001 respectively, ANCOVA test).

The regression lines of Group 22 (3 hours after the administration of isosorbitol+sodium alginate) and Group 5 (6 hours after the administration of isosorbitol+sodium alginate) further shift downward. The differences between these groups and the control group were significant (p<0.001 and p<0.001 respectively, ANCOVA test), and thus the decompression effect proved more remarkable. Comparing the effect of the combination of isosorbitol and sodium alginate with that of conventional one, 3 hours after the administration, the decompression effect in Group 22 was significantly remarkable compared with that of conventional isosorbitol (Group 20) (p<0.01, ANCOVA test). On the other hand, 6 hours after the administration, no significant difference was present between Group 23 and conventional isosorbitol (Group 21) (ANCOVA test).

These results indicate that the decompression effect of isosorbitol added sodium alginate appeared 3 hours after the administration (p<0.001) and lasted till r 6 hours the administration or later (p<0.001). Comparing with conventional one, the decompression effect appears significantly remarkable 3 hours after the administration (p<0.01), suggesting prompt onset of its therapeutic effect.

Six hours after, although the difference is not significant, the regression line shifts downward comparing to the conventional one. Also it can be clearly understood from the condition of feces and the generation of gas in the gastrointestinal tract that the gastrointestinal symptoms including cathartic effect are successfully improved. Therefore, sufficient therapeutic results may be achieved with fewer amounts of additives without stress or irritation on the gastrointestinal tract.

It is now found that diarrhea caused by the administration of saccharides or sugar alcohols can be inhibited by adding polysaccharides to those. In order to examine whether this advantage is characteristic of the combination of saccharides or sugar alcohols and polysaccharides, polyvinylpyrrolidone (Reference Example 6) and jelly (Reference Example 7), which are generally used as emulsifiers, suspending agents or thickners as polysaccharides, are used instead of polysaccharides to examine antidiarrheal effect thereof.

Reference Example 6

Erythritol Added Polyvinylpyrrolidone

Guinea pigs (280 to 350 g of body weight, normal feces) received the surgical obliteration of the endolymphatic sac in the left ear to prepare an "animal model of experimental endolymphatic hydrops". The surgery was performed as previously described in Non-patent Reference 8.

One month after, the animals orally received erythritol (2.8 g/kg) added polyvinylpyrrolidone (0.5 g/kg, about 7.1% by weight). The conditions of feces were observed for 6 hours. 3 hours after, animals were sacrificed and the samples were observed to assess its decompression effect as described hereinbefore (Table 40). The result is shown in FIG. 10 with comparing Group 4 in Example 2 (Animals were sacrificed 3 hours after the administration of erythritol 2.8 g/kg alone).

Figure 10:
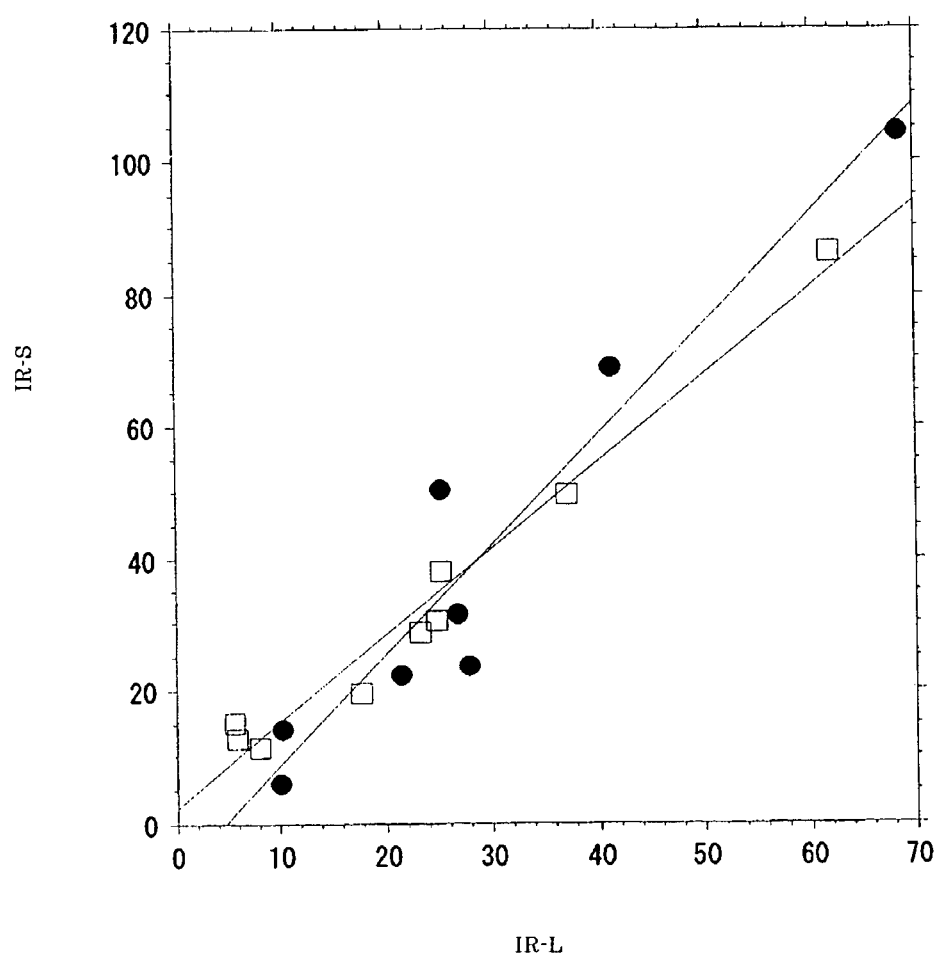
FIG. 10 indicates the IR-L and IR-S of the group administering erythritol added polyvinyl pyrrolidone (a thickner) and the group administering erythritol alone in Reference Example 6.

FIG. 10 indicates correlation between the membrane extending rate (horizontal axis) and the area increasing rate (vertical axis) in operated side as a scattergram and regression lines in each animals. In FIG. 10, □ (opening square): IR-S (3 hours after the administration of erythritol alone) vs IR-L (3 hours after the administration of erythritol alone), ● (filled circle): IR-S (3 hours after the administration of erythritol added thickner) vs IR-L (3 hours after the administration of erythritol added thickner). The regression lines are IR-S (3 hours after the administration of erythritol alone)=2.407+1.309* IR-L (3 hours after the administration of erythritol alone); R2=0.974, IR-S (3 hours after the administration of erythritol added thickner)=−7.511+1.659*IR-L (3 hours after the administration of erythritol added thickner); R2=0.916, respectively.

The difference between the present group and Group 4 is not significant, suggesting that no decompression effect is produced by adding a thickner to erythritol.

TABLE 40

| Saccharide or sugar alcohol | Dosage | Additives | | Number of animals | Hardness of feces | | | |
|---|---|---|---|---|---|---|---|---|
| | | | | | 3 | 2 | 1 | 0 |
| Erythritol* | 2.8 g/kg | — | — | 5 | 0 | 0 | 0 | 5 |
| Erythritol | 2.8 g/kg | PVP | 0.2 g/kg | 5 | 0 | 0 | 0 | 5 |

Erythritol* Group 4 in Example 2

Two hours after the administration, muddy feces were shown in 3 animals out of 5. Three hours after, muddy feces were shown in all animals. The stage of diarrhea was more serious than that caused by erythritol.

FIG. 10 indicates correlation between IR-L (horizontal axis) and IR-S (vertical axis) in operated side as a scatter diagram and regression lines in each of the animals. The difference between the present group and Group 4 is not significant, suggesting that no decompression effect is produced by adding a thickner to erythritol.

Reference Example 7

Erythritol or Isosorbitol Added Jelly

As described hereinbefore, erythritol or isosorbitol as saccharides or sugar alcohols added jelly as a thickner were orally administered to 10 guinea pigs (280 to 350 g body weight) as shown in Table 41. The conditions of feces were observed. Three hours after, animals were sacrificed and observed the condition in the gastrointestinal tract.

TABLE 41

| Agent | Dosage | Additives | Dosage | Number of animals | Hardness of feces | | | |
|---|---|---|---|---|---|---|---|---|
| | | | | | Normal | Slightly soft | Soft | Muddy |
| Erythritol** | 2.8 g/kg | — | — | 5 | 0 | 0 | 0 | 5 |
| Erythritol | 2.8 g/kg | Jelly | 0.05 g/kg | 5 | 0 | 0 | 0 | 5 |
| Erythritol | 2.8 g/kg | Jelly | 0.1 g/kg | 5 | 0 | 0 | 0 | 5 |
| Erythritol | 2.8 g/kg | Jelly | 0.15 g/kg | 5 | 0 | 0 | 0 | 5 |
| Isosorbitol* | 2.8 g/kg | Jelly | — | 8 | 2 | 2 | 3 | 1 |
| Isosorbitol | 2.8 g/kg | Jelly | 0.1 g/kg | 5 | 2 | 0 | 2 | 1 |
| Isosorbitol | 2.8 g/kg | Jelly | 0.25 g/kg | 5 | 2 | 0 | 3 | 0 |

Erythritol* Group 4 in Example 2

Isosorbitol* Example 1-d, Reference Example 4

In the group administered with erythritol added jelly, 2 hours after the administration, soft feces were shown in a part of animals and 3 hours after, muddy feces were shown in all animals. The diarrhea was as severe as that in the group administered with erythritol alone.

In the group administered with isosorbitol added jelly, feces gradually softened over time, and muddy or soft feces were shown in almost half of the animals 3 hours after the administration. The diarrhea was as severe as that in the group administered with isosorbitol alone, i.e. no significant difference. In both combinations, no antidiarreal effect by jelly was shown These results suggest that polysaccharides are required to improve and/or inhibit the noxious gastrointestinal symptoms caused by saccharides or sugar alcohols.

Reference Example

The decompression effect on endolymphatic hydrops of polysaccharides itself was morphologically investigated. Firstly, 5 guinea pigs received the surgical obliteration of the endolymphatic sac in the left ear. One month after, plain pectin as polysaccharides was orally administered at 0.5 g/kg, confirming their normal feces. Three hours after the administration animals were sacrificed. The surgical obliteration of the endolymphatic sac, the process for sample preparation and the measurements were carried out as described hereinbefore.

Effect of pectin on digestive organs and effect of decompression of endolymphatic hydrops

TABLE 42

| Agent | Dosage | Time from administration to perfusion | Number of animals | Length of formed feces | Hardness of feces | | | | | Space | | | |
|---|---|---|---|---|---|---|---|---|---|---|---|---|---|
| | | | | | Hard | Normal | Slightly soft | Soft | Muddy | Regular | Irregular | Extraordinary | Muddy |
| pectin | 0.5 g/kg | 3 hours | 5 | 58.6 ± 9.7 | 0 | 5 | 0 | 0 | 0 | 5 | 0 | 0 | 0 |

TABLE 43

| IR-L (%) | IR-S (%) |
|---|---|
| 36.3 ± 23.3 | 48.2 ± 29.2 |

Figure 11:
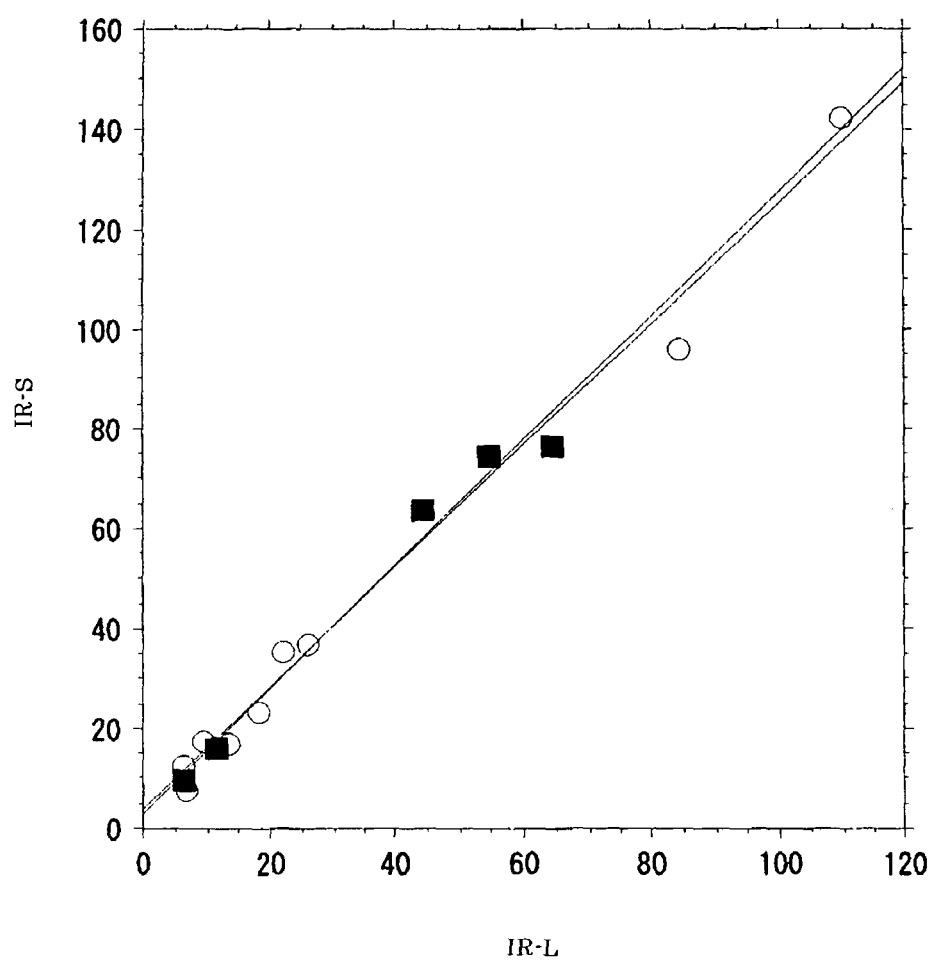
FIG. 11 indicates the IR-L and IR-S of the group administering pectin alone compared with those in a control group (distilled water) in Reference Example.

In consequence, normal feces were shown in all 5 animals and the spaces were regular. The scatter diagram and the regression line of the length of membrane (IR-L) and increase rate of the area of the scala media (IR-S) were calculated according to the method described in Example 2 (FIG. 11). Comparing with the regression line in control group, both of two lines nearly overlap, i.e. no significant difference is ascertained. This result indicates that polysaccharides itself has no endolymphatic hydrops decompression effect.

In FIG. 11, ○ (opening circle): IR-S (control) vs IR-L, ■ (filled square): IR-S (pectin alone) vs IR-L (pectin alone). The regression lines are IR-S (control)=4.011+1.212*IR-L (control) line 1; R2=0.987, IR-S (pectin alone)=3.018+1.244*IR-L (pectin alone); R2=0.979, respectively.

EXAMPLE 4

Volume of Agent

When erythritol is administered to an adult (60 kg body weight), the single dose may be 10 to 80 g, preferably 20 to 60 g. When 21 g of erythritol is administered as powder, the volume may be about 53 ml. Alternatively, administered as saturated aqueous solution, it requires 65 ml of distilled water, and volume and weight thereof is 78 ml and 86 g, respectively. Carrying it to administer 3 times daily is inconvenient for a patient with Meniere's disease. The gel formulation of the present invention has significantly reduced its volume and weight as shown hereinafter.

Formulation Example 1

| Erythritol | 21 g |
|---|---|
| Pectin | 3.75 g |
| Distilled water | 11.25 ml |

The volume of this gel formulation is 20.25 ml and the weight thereof is 36 g. By drying and grinding this gel formulation, the volume increases to 33 ml, however it is convenient for carrying. The particle size of dry milled powder is described in Table 44. If water (10 ml) is added thereto prior to use and mixed, a gel formulation (23 ml) is again obtained.

Formulation Example 2

| Erythritol | 21 g |
|---|---|
| Xanthan gum | 0.25 g |
| Distilled water | 3.75 ml |

The volume of this gel formulation is 20.25 ml and the weight thereof is 26.1 g. By drying and grinding this gel formulation, the volume increases to 31.5 ml. The particle size of dry milled powder is described in Table 44. If water (3 ml) is added thereto prior to use and mixed, a gel formulation (24 ml) is again obtained.

TABLE 44

| | Change of formulation and volume | | | | | | |
|---|---|---|---|---|---|---|---|
| | Volume after mixing (ml) | Weight after mixing (g) | Volume after grinding (ml) | Particle size after grinding (0.01 mm) | | | Volume after regelation (ml) |
| Formulation 1 | 20.25 | 36 | 33 | less than 7 4.9 ml | 7 to 10 6.2 ml | more than 10 24.9 ml | 23.25 |
| Formulation 2 | 20.25 | 26.1 | 31.5 | up to 5 11.2 ml | more than 5 14.9 ml | | 24.0 |

In both formulations of 1 and 2, the volume and the weight of the gel formulations were significantly reduced to about fourth and third of those of erythritol saturated solution. Therefore, the gel formulation is convenient for carrying and easy for administering.

The volume of an isosorbide formulation which is currently available in Japan is 30 ml and the weight thereof is 40.5 g (isosorbitol content: 21 g). The volume and weight of the gel formulation of the present invention is about two-thirds against those of conventional formulation.

Patients feel inconvenience for the conventional isosorbide formulation in its characteristic bitterness, as well as its difficulty for carrying and storing the liquid in a 500 ml bottle (about 700 g). The gel formulation of the present invention can be dried and grinded to the powder formulation and then, if necessary, it may easily be granulated. Therefore, the preparation of the present invention in powder or granule form can be carried in an amount as desired number of doses. Also, the powder or granule may immediately form gel formulation by adding distilled water, for example prior to administering to a patient. Therefore, the formulation of the present invention is convenient.

What is claimed is:

1. A method for treating Meniere's disease comprising administering to a patient suffering from Meniere's disease a therapeutically effective amount of a pharmaceutical composition comprising the following components:
    (a) an amount of at least one compound selected from glycerol, erythritol, xylitol, xylose, and isosorbitol sufficient to treat Meniere's disease, and
    (b) at least one compound selected from polysaccharides, Wherein:

A ratio by weight of the component (a) to the component (b) is about 100:2 to 100:50;

If component (a) is isosorbitol at 100 parts by weight, then component (b) is not locust bean gum and/or xanthan gum at 2 parts by weight; and If component (a) is isosorbitol and component (b) is agar, the ratio by weight of the component (a) to the component (b) is about 100:10 to 100:50.

2. The method for treating Meniere's disease according to claim 1, wherein the ratio by weight of the component (a) to the component (b) is about 100:5 to 100:50.

3. The method for treating Meniere's disease according to claim 1, wherein the ratio by weight of the component (a) to the component (b) is about 100:10 to 100:40.

4. The method for treating Meniere's disease according to claim 1, wherein the component (a) is erythritol, xylitol or isosorbitol.

5. The method for treating Meniere's disease according to claim 4, wherein the component (a) is isosorbitol.

6. The method for treating Meniere's disease according to claim 1, wherein the component (b) is selected from pectin, xanthan gum, guar gum, gum arabic, locust bean gum, tara gum, sodium alginate, sodium carboxymethyl cellulose, hydroxypropyl cellulose, agar and carrageenan.

7. The method for treating Meniere's disease according to claim 6, wherein the component (b) is selected from pectin, xanthan gum, sodium alginate, sodium carboxymethyl cellulose and agar.

8. The method for treating Meniere's disease according to claim 7, wherein the component (b) is pectin and/or xanthan gum.

9. The method for treating Meniere's disease according to claim 1, wherein the pharmaceutical composition is in a gel form.

10. The method for treating Meniere's disease according to claim 9, wherein a water content of the gel is about 10 to 55% by weight based on the total amount of the components (a) and (b).

11. The method for treating Meniere's disease according to claim 1, wherein the pharmaceutical composition is in a powder form.

12. The method for treating Meniere's disease according to claim 1, wherein the pharmaceutical composition is in a granule form.

13. A method for preparing a pharmaceutical composition in powder form for treating Meniere's disease, comprising:

adding water to a component (a), which is at least one compound selected from glycerol, erythitol, xylitol, xylose and isosorbitol and a component (b), which is at least one compound selected from polysaccharides;

mixing the component (a), the component (b) and the water to obtain a gel; and drying and grinding the gel;

wherein;

a ratio by weight of the component (a) to the component (b) is about 100:2 to 100:50;

a water content of the gel is about 10 to 55% by weight based on a total amount of the components (a) and (b);

if component (a) is isosorbitol at 100 parts by weight, then component (b) is not locust bean gum and/or xanthan gum at 2 parts by weight; and if component(a) is isosorbitol and component (b) is agar, the ratio by weight of the component (a) to the component (b) is about 100:10 to 100:50.

14. A method for preparing a pharmaceutical composition in granule form for treating Meniere's disease, comprising:

adding water to a component (a), which is at least one compound selected from glycerol, erythitol, xylitol, xylose and isosorbitrol and a component (b), which is at least one compound selected from polysaccharides;

mixing the component (a), the component (b) and the water to obtain a gel;

drying and grinding the gel to obtain a powder; and granulating the powder;

wherein;

a ratio by weight of the component (a) to the component (b) is about 100:2 to 100:50;

a water content of the gel is about 10 to 55% by weight based on a total amount of the components (a) and (b);

if component (a) is isosorbitol at 100 parts by weight, then component (b) is not locust bean gum and/or xanthan gum at 2 parts by weight; and if component (a) is isosorbitrol and component (b) is agar, the ratio by weight of the component (a) to the component (b) is about 100:10 to 100:50.

* * * * *